(12) United States Patent
Gianchandani et al.

(10) Patent No.: US 8,467,867 B2
(45) Date of Patent: Jun. 18, 2013

(54) IN-SITU TISSUE ANALYSIS DEVICE AND METHOD

(75) Inventors: Yogesh B. Gianchandani, Ann Arbor, MI (US); Tao Li, Ann Arbor, MI (US); Roma Y. Gianchandani, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/088,673

(22) Filed: Apr. 18, 2011

(65) Prior Publication Data

US 2011/0196259 A1   Aug. 11, 2011

Related U.S. Application Data

(63) Continuation of application No. 11/625,801, filed on Jan. 22, 2007, now Pat. No. 7,927,288.

(60) Provisional application No. 60/760,700, filed on Jan. 20, 2006.

(51) Int. Cl.
*A61B 5/05* (2006.01)

(52) U.S. Cl.
USPC .......................................... 600/547; 600/561

(58) Field of Classification Search
USPC .................. 600/534, 561, 547; 73/599
See application file for complete search history.

(56) References Cited

U.S. PATENT DOCUMENTS

| | | | |
|---|---|---|---|
| 3,710,781 A * | 1/1973 | Huthcins et al. ............ | 600/488 |
| 4,535,773 A * | 8/1985 | Yoon ............................ | 606/185 |
| 5,060,658 A | 10/1991 | Dejter, Jr. et al. | |
| 5,209,721 A * | 5/1993 | Wilk ............................ | 604/26 |
| 5,320,101 A | 6/1994 | Faupel et al. | |
| 5,383,465 A | 1/1995 | Lesny et al. | |
| 5,520,189 A | 5/1996 | Malinowski et al. | |
| 5,634,464 A * | 6/1997 | Jang et al. .................... | 600/467 |
| 6,108,439 A | 8/2000 | Ishiguro | |
| 6,109,270 A * | 8/2000 | Mah et al. .................... | 606/130 |
| 6,564,087 B1 | 5/2003 | Pitris et al. | |
| 6,612,190 B2 * | 9/2003 | Takeuchi et al. ............. | 73/865 |
| 6,629,343 B1 | 10/2003 | Chesney et al. | |
| 6,847,841 B1 | 1/2005 | El Hatw | |
| 6,869,430 B2 | 3/2005 | Balbierz et al. | |
| 6,912,759 B2 | 7/2005 | Izadnegahdar et al. | |
| 7,331,236 B2 | 2/2008 | Smith et al. | |
| 2002/0026188 A1 | 2/2002 | Balbierz et al. | |
| 2002/0115198 A1 | 8/2002 | Nerenberg et al. | |
| 2003/0018273 A1 | 1/2003 | Corl et al. | |
| 2004/0102733 A1 | 5/2004 | Naimark et al. | |
| 2005/0261568 A1 * | 11/2005 | Hular et al. ................. | 600/407 |
| 2007/0078484 A1 | 4/2007 | Talarico et al. | |

OTHER PUBLICATIONS

Chang et al., "In-situ Rock Probing Using the Ultrasonic/Sonic Driller/Corer (USDC)," *Proceedings of SPIE*, 5056:567-573 (2003).

(Continued)

*Primary Examiner* — Max Hindenburg
*Assistant Examiner* — Renee Danega
(74) *Attorney, Agent, or Firm* — Marshall, Gerstein & Borun LLP

(57) ABSTRACT

A sensor is mounted to a needle at a location proximate to a tip of the needle. The sensor senses tissue density of tissue in contact with the tip as the needle passes through the tissue. Further, the sensor detects a change in tissue density as the tip passes from one tissue to a target tissue.

25 Claims, 24 Drawing Sheets

OTHER PUBLICATIONS

Feng et al., "Fabrication of MEMS ZnO Dome-Shaped-Diaphragm Transducers for High-Frequency Ultrasonic Imaging," *J. Micromech. Microeng.*, 15:586-590 (2005).

Li et al., "A Die-Scale Micromachining Process for Bulk PZT and its Application to In-Plane Actuators," *Proc. IEEE MEMS*, pp. 387-390 (2005).

Li et al., "A Micromachining Process for Die-Scale Pattern Transfer in Ceramics and its Application to Bulk Piezoelectric Actuators," *IEEE/ASME J. Microelectromechanical Systems*, 15(3): 605-612 (2006).

Li et al., "LEEDUS: A Micromachining Process for Die-Scale Pattern Transfer in Ceramics with High Resolution and Throughput," *Tech. Digest Hilton Head*, pp. 324-327 (2004).

Zhang et al., "Micromachined Acoustic Resonant Mass Sensor," *J. Microelectromechanical Systems*, 14(4):699-706 (2005).

\* cited by examiner a: 1%, 2% & 3.5% saline; b: Porcine muscle;
c: Porcine fat; d: Babyoil; e: Mineral oil; f: Peanut oil.

IN-SITU TISSUE ANALYSIS DEVICE AND METHOD

CROSS-REFERENCE TO RELATED APPLICATION

The present application is a continuation, and claims the benefit, of U.S. patent application Ser. No. 11/625,801, entitled "In-Situ Tissue Analysis Device and Method," filed Jan. 22, 2007, and also claims the benefit of U.S. Provisional Application No. 60/760,700, entitled "IN-SITU TISSUE ANALYSIS DEVICE AND METHOD," filed on Jan. 20, 2006. Each of these applications is hereby incorporated by reference herein in its entirety for all purposes.

STATEMENT REGARDING FEDERALLY SPONSORED RESEARCH OR DEVELOPMENT

This invention was made with government support under Contract No.: EEC-9986866 awarded by the National Science Foundation. The government has certain rights in the invention.

BACKGROUND OF THE DISCLOSURE

1. Field of the Disclosure

The disclosure relates generally to tissue analysis and, more particularly, to sensor devices capable of in-situ tissue analysis, such as tissue contrast or differentiation in connection with, for instance, fine needle aspiration biopsy procedures.

2. Brief Description of Related Technology

Clinical diagnosis of thyroid cancer can be very challenging, inasmuch as malignant tumors need to be differentiated from benign nodules. With ultrasound characteristics of benign and malignant nodules being similar, fine needle aspiration (FNA) biopsy is typically relied upon for final diagnosis of the thyroid nodules, which are observed in about 20% of the general U.S. population. With the small size of the nodules. FNA biopsy is typically performed with a 20-27 gauge needle attached to a 10 mL syringe for suction of thyroid tissue, which is then examined by a cytologist.

The fine needles used in FNA biopsy procedures make precise sampling possible. Specifically, typical needle sizes allow the biopsy tool to be used in close proximity to areas that should not be disturbed or touched. Collateral damage to nearby regions that may otherwise be caused by insertion of larger needles is then hopefully minimized.

Despite these potential advantages, the FNA biopsy procedure is challenging in itself because of the precision required in recovering a sample from the small target volumes. To aid this, conventional ultrasound imaging is performed in real time, especially for those nodules that are difficult to palpate or contain complicated solid and cystic areas. Past attempts to provide such real-time guidance via such imaging alone have introduced significant complexity, requiring special training and equipment that only limited hospitals can afford, yet are not always effective. At least 2-5% of FNA biopsies are read as non-diagnostic because of improper sampling.

SUMMARY OF THE DISCLOSURE

In one embodiment, an apparatus comprises a biopsy needle having a tip, and a sensor mounted to the needle at a location proximate to the tip. The sensor senses properties of tissue in contact with the sensor and proximate to the tip. The apparatus also comprises a communication link coupled to the sensor, the communication link to communicatively couple the sensor with a system interface.

In another embodiment, a method for obtaining a biopsy includes inserting a biopsy needle in a patient, the biopsy needle including a sensor mounted at a location proximate to a tip of the needle, the sensor to sense properties of tissue in contact with the sensor and proximate to the tip. The method also includes monitoring properties of tissue immediately proximate to the tip while guiding the tip toward a target tissue, the properties sensed by the sensor. Additionally, the method includes determining when to obtain a biopsy based on changes in tissue properties sensed by the sensor, and extracting a biopsy from the target tissue.

In yet another embodiment, a method for providing real-time guidance during a biopsy comprises sensing, during a biopsy procedure, properties of tissue immediately proximate to a tip of a biopsy tool using a sensor mounted at a location proximate to the tip, and indicating the sensed tissue properties during the biopsy procedure to facilitate positioning of the tip within a target tissue.

In still another embodiment, an apparatus comprises a biopsy needle having a tip, and a sensor mounted to the needle at a location proximate to the tip. The sensor senses properties of tissue in contact with the sensor and proximate to the tip.

DETAILED DESCRIPTION OF PREFERRED EMBODIMENTS

Figure 1:
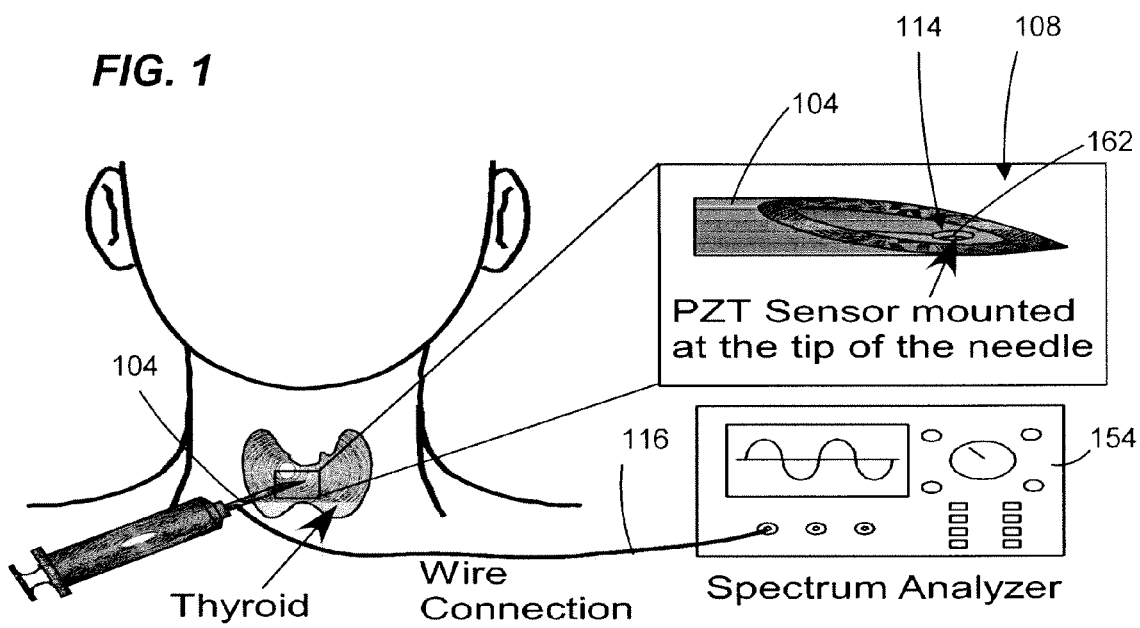
FIG. 1 is a block diagram of a biopsy device.

Disclosed herein are devices and methods generally directed to in-situ tissue analysis, which may, in some cases, be conducted in conjunction with biopsy procedures such as fine needle aspiration (FNA) biopsy. The disclosed devices and methods utilize techniques well suited for a variety of tissue analysis contexts involving tissue contrast sensing or differentiation, including those contexts in which the tissue region targeted by the analysis is very small. As described below, the disclosed devices and methods provide a high degree of precision in discriminating between the target and surrounding tissues, which may be useful when the target volume is not much larger than the tool utilized to biopsy or analyze the tissue.

In some cases, the disclosed devices and methods may generally be used to provide real-time guidance for biopsy procedures to supplement or otherwise improve upon the information provided by imaging techniques, such as ultrasound or RF imaging techniques. As shown below, the disclosed devices and methods provide tissue contrast and differentiation information of a more current, local, precise and immediate nature than imaging techniques, insofar as the sensed tissue characteristics are associated with the tissue located at or very near the tip or end of the biopsy needle or tool.

Although well suited for use in biopsy procedures (e.g., FNA biopsy), practice of the disclosed methods and devices is not limited to tissue removal or sampling contexts. On the contrary, the disclosed methods and devices may be advantageously utilized in any in-situ tissue analysis context, application, or other procedure that may benefit from such analysis, especially when such analysis involves or benefits from resolution on the cellular scale. In this way, applications that involve cytological analysis may rely upon the disclosed methods and devices where past sensing tools were either too large, crude or otherwise imprecise to sense tissue characteristics at such small scales.

The precision performance and resulting precise analysis of the disclosed device and method are generally enabled by the nature and deployment of an integrated sensing device. The integrated sensing device includes a sensing element or structure the dimensions of which enable it to be disposed very near the apex, point or end of the device (e.g., needle) introduced into the tissue, thereby allowing it to resolve targets of a similar or smaller size than the needle aperture. To this end, one or more components of the disclosed device may be micromachined or otherwise fabricated to have feature sizes at the micro-scale, as described below.

In some embodiments, the needle aperture may be on the order of about 1 mm. Despite the small size of the needle, current biopsy practices may refrain from acting upon nodules and other elements smaller than about 7-8 mm, due to the current resolution limits of MRI and other preliminary imaging procedures relied upon to make the decision whether to proceed with a biopsy. However, the analysis provided by the disclosed devices and methods can be more precise than the current practice limits. Accordingly, practice of the disclosed methods and devices is not limited to current biopsy practices and may instead be used when improved imaging techniques are developed in the future to support preliminary detection of smaller nodules and other elements. Moreover, to the extent that practical limits were placed on the resolution provided by the preliminary imaging procedures, in the sense that a low resolution may make tissue discrimination more difficult, practice of the disclosed devices and methods may be used to provide useful detection and precision.

In accordance with one aspect of the disclosure, a tissue sensor has a needle or other structural element capable of penetration for in-situ deployment, and a sensing element having a sufficiently small size to be disposed at a position on the structural element at or near an end thereof such that the sensing element can enable or support cytological analysis of the tissue in contact with the end of the structural element.

The sensing element may be embedded in a wall of the needle or structural element. Alternatively, the sensing element may be disposed on a surface of the needle or structural element. In either case, the sensing element may be disposed in a cavity or interior of the needle or structural element through which a sample passes for collection (e.g., biopsy).

In some embodiments, the sensing element may include a micromachined structure. Alternatively or additionally, the needle or structural element may be micromachined to accommodate the sensing element.

Generally speaking, the tissue sensor may implement mechanical, electrochemical or electrical sensing schemes. Mechanical sensing schemes include, for example, acoustic-, pressure- or piezoelectric-based sensing. Electrochemical sensing schemes may be potentiometric or amperometric. Electrical sensing schemes may involve a resistance or impedance measurement between the sensing element and another electrode of the tissue sensor. In each of the sensing schemes, the sensing element senses a tissue characteristic through contact with the tissue being analyzed.

The sensing and discrimination provided by the disclosed tissue sensor may be performed in conjunction with an FNA biopsy procedure, in which case the needle or structural element may be a syringe needle to collect a tissue volume. Subsequent cytological analysis is therefore location-specific. In these cases, the configuration of the disclosed tissue sensor is advantageous because the apparatus handling the collection is in contact with the same tissue (i.e., tissue volume or region) being sensed. In this way, the sensing functionality provided by the disclosed tissue sensor provides real-time guidance of a highly local and immediate nature to the biopsy procedure.

To these ends, the structural element may include a 20-27 gauge needle, such that the outer diameter of the needle is about 1 mm in diameter or smaller and the size or region from which the sample is drawn is about 3 mm or smaller. In some embodiments, micromachined needles or needle arrays may be employed in conjunction with the disclosed devices and methods.

In accordance with another aspect of the disclosure, a biopsy tool includes a needle having an interior region through which the biopsy sample passes for collection, and a sensor disposed in or near the interior region to provide in-situ tissue characterization. In this way, the biopsy tool provides a single structure for performing both the biopsy function and for providing real-time guidance via the in-situ tissue characterization.

In accordance with yet another aspect of the disclosure, a method is useful for providing real-time guidance during biopsy of a target tissue volume or region using a tool having an integrated sensor in contact with the target tissue volume during operation. The disclosed method includes the following steps:

(i) positioning or moving the tool in an approach toward the target tissue volume;

(ii) monitoring a tissue characteristic based on data provided by the integrated sensor during the positioning step; and, (iii) determining when to obtain a biopsy sample based on a change in the tissue characteristic.

In some cases, the change in the tissue characteristic may include or involve reaching a maximum or minimum value of the tissue characteristic. In this way, the monitoring step may include or involve following a gradient in the tissue characteristic as a guide toward the target tissue volume.

The method may further include monitoring an image provided by ultrasound or any other RF imaging technique for additional guidance. The imaging technique may provide information of a broader, more general or forward-looking nature, while the information provided via the tissue characteristic would provide, in comparison, more local and/or immediate feedback of the nature of the tissue at the current position of the tool.

In some embodiments, the disclosed method may use a tool having multiple sensors directed to sensing the same tissue characteristic. At one level, the multiple sensors provide redundancy in operation. In some cases, however, the method may include processing the data provided by the multiple sensors to remove common mode or other noise. In this way, the signal processing of the disclosed method with multiple sensors may provide differential sensing useful for detecting small changes in the tissue characteristic, such as when the target tissue does not differ markedly from the surrounding tissue.

The design, fabrication and integration of a sensor near the tip of a conventional syringe needle or other biopsy tool is described below. Such integration may assist in a variety of procedures, including without limitation FNA biopsy. In the FNA of cancerous nodules or biopsy of other very small tumors, it can be challenging to simply locate the tumor with the biopsy needle. Real time information on tissue parameters can provide the physician with immediate feedback in locating the correct region, thereby reducing the likelihood of an inconclusive diagnosis or the need to remove large volumes of tissue. To this end, a biopsy needle is described that can detect different tissue planes or variations of densities (e.g., solid vs. cystic), thereby making the detection of thyroid cancer (or other easily cured cancers) not only more accurate, but more widely accessible. In one example described below, a piezoelectric sensor is located within a needle for FNA of thyroid biopsies. The device has been tested using natural and synthetic materials that mimic the texture and ultrasound signature of human tissue in the training of physicians, and also tested with porcine fat and muscle tissue. The description of the exemplary sensor is provided with the understanding that other types of sensors, including sensors for pressure, temperature, pH, resistance, etc., can alternatively or additionally be integrated to provide a wide range of local tissue characteristics of interest in various medical procedures. Some embodiments may also include optical sensing in combination with one or more of the other techniques, such that one or more optical sensors or devices may also be integrated to any desired extent.

The exemplary piezoelectric sensor is integrated into a cavity at the tip of a biopsy needle intended for fine needle aspiration (FNA) of thyroid nodules. Located on a steel diaphragm of 300 μm radius and 23 μm average thickness, it is intended to aid in tissue differentiation, providing information that may be complementary to any imaging method that may be used concurrently. The sensor may be fabricated from bulk lead zirconate titanate (PZT) using the process described below. Specifically, micro electro-discharge machining is used to form a steel tool that is subsequently used for batch-mode ultrasonic machining of bulk PZT ceramic. The resulting sensor is 50 μm thick and 200 μm in diameter. Devices were tested in materials that mimic the texture of human tissue in the training of physicians, and were separately tested with porcine fat and muscle tissue. The magnitude and frequency of a resonant peak shows tissue-specific characteristics as the needle is inserted into tissue. For example, in the porcine tissue sample, the magnitude and peak frequency respectively change from ≈2118Ω and ≈163 MHz to ≈562Ω and ≈150 MHz as the needle moves from fat to muscle tissue.

With reference now to FIG. 1, it illustrates an example biopsy system 100. The system 100 includes a biopsy needle 104 having a tip 108. A piezoelectric sensor 112 is integrated into a cavity 114 at the tip 108 of the biopsy needle 104. The needle 104 may be a needle suitable for fine needle aspiration (FNA) of thyroid nodules, for example. The sensor 112 is fabricated from bulk lead zirconate titanate (PZT) using a customized process. Micro electro-discharge machining (μEDM) is used to form a steel tool that is subsequently used for batch-mode micro ultrasonic machining (μUSM) of bulk PZT ceramic. The devices are tested in materials that mimic the texture of human tissue in the training of physicians, and were separately tested with porcine fat and muscle tissue.

Design and Fabrication. Piezoelectric materials such as piezoelectric ceramics (PZT series, etc.), polymers (PVDF, etc.), quartz, and ZnO, have been widely used in the fabrication of sensors and actuators. See Zhang, et al., "Micromachined acoustic resonant mass sensor," *IEEE/ASME J. Microelectromechanical Systems*, 14(4), pp. 699-706 (2000); and, Feng, et al., "Fabrication of MEMS ZnO dome-shaped-diaphragm transducers for high frequency ultrasonic imaging," *J. Micromechanics and Microengineering*, 15(3), pp. 586-590 (2005). PZT is of particular interest for MEMS applications due to its high piezoelectric coefficients and good electro-mechanical coupling. When the mechanical boundary condition of a PZT-horn assembly changes by touching different types of rock materials, the resonance frequency and the electric impedance of the assembly change accordingly. See Chang, et al., "In-situ rock probing using the ultrasonic/sonic driller/corer," *Proc. SPIE Smart Structures Conference*, San Diego (2003).

Figure 2A:
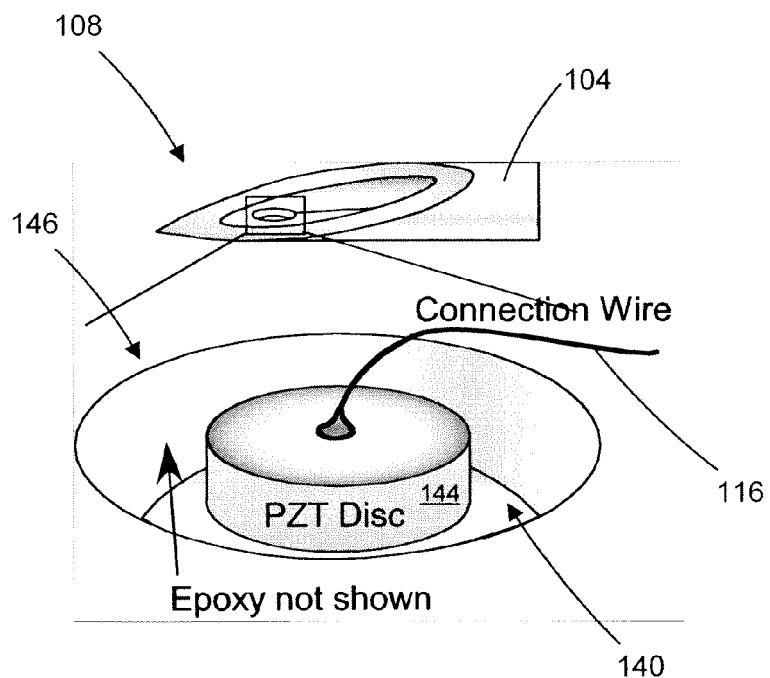
FIGS. 2(a) and 2(b) are block diagrams of a bulk lead zirconate titanate (PZT) sensor mounted proximate to a tip of a biopsy needle.
Figure 2B:
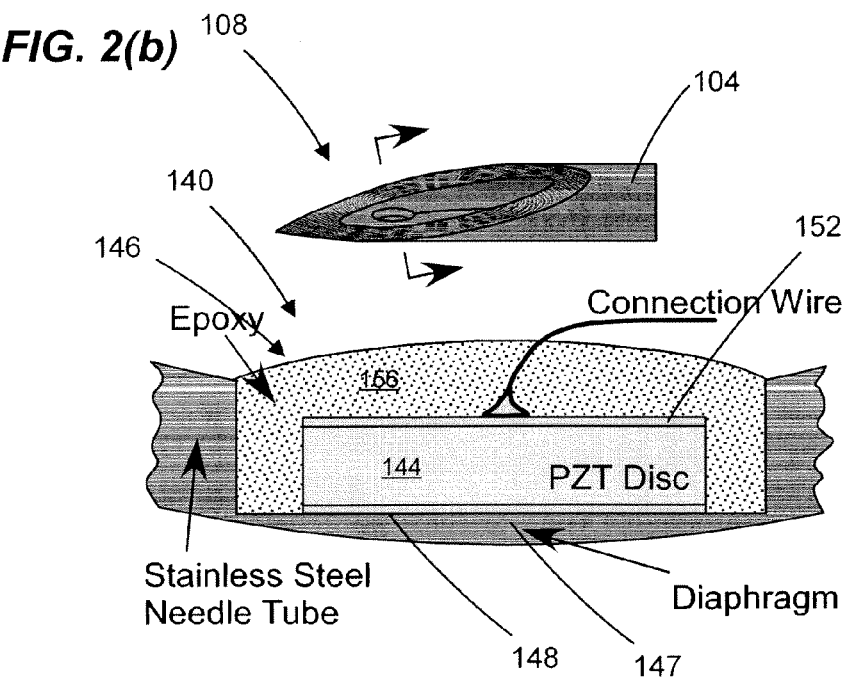

The exemplary scheme for in-situ detection of tissue contrast during thyroid biopsy is shown in FIG. 1. The PZT sensor 112 mounted at the tip 108 of the needle 104 is coupled to a spectrum analyzer 120 for real-time impedance measurement. FIGS. 2(a) and 2(b) illustrate an example sensor 140. The sensor 140 includes a PZT disc 144 located within a cavity formed in the needle 104 proximate to the tip 108. The PZT disc 144 is located against a diaphragm 147 and within a cavity 146 micromachined into the wall of the needle 104. The diaphragm 147 also serves as a ground plane for one electrode 148 of the sensor 140. A second electrode 152, which is coupled to the top of the PZT disc 144, is coupled to a flexible insulated wire 116 that extends along the lumen of the needle 104. Since the diaphragm 147 makes contact with the tissues encountered during a biopsy procedure, and the tissue types have different acousto-mechanical impedance, the vibration characteristics of the diaphragm 147 and the PZT disc 144 will change accordingly. This change in mechanical resonance is transduced to a change in electric impedance of the PZT disc 144 by the piezoelectric effect and can be detected by the impedance spectrum analyzer 120, for example. Thus, the changes in the electric impedance provide a measure of tissue contrast in this preliminary version of the sensor. The cavity 146 is filled with an epoxy 156.

This PZT sensor 140 is designed to respond to tissue that is in contact with the diaphragm 147 and in close proximity of the probe as it is inserted during a biopsy procedure. Different tissue types have different density and elastic properties. The mass loading and elastic loading to the diaphragm 147, and thereby the vibration characteristics of the diaphragm 147, change accordingly. This changes the mechanical boundary conditions of the PZT disc 144, which is transduced into a change of electrical impedance by the piezoelectric effect, and subsequently detected by an impedance spectrum analyzer 120, for example, thus providing a measure of tissue contrast. For example, a change in the frequency of an impedance resonance peak may indicate a tissue contrast.

Figure 3:
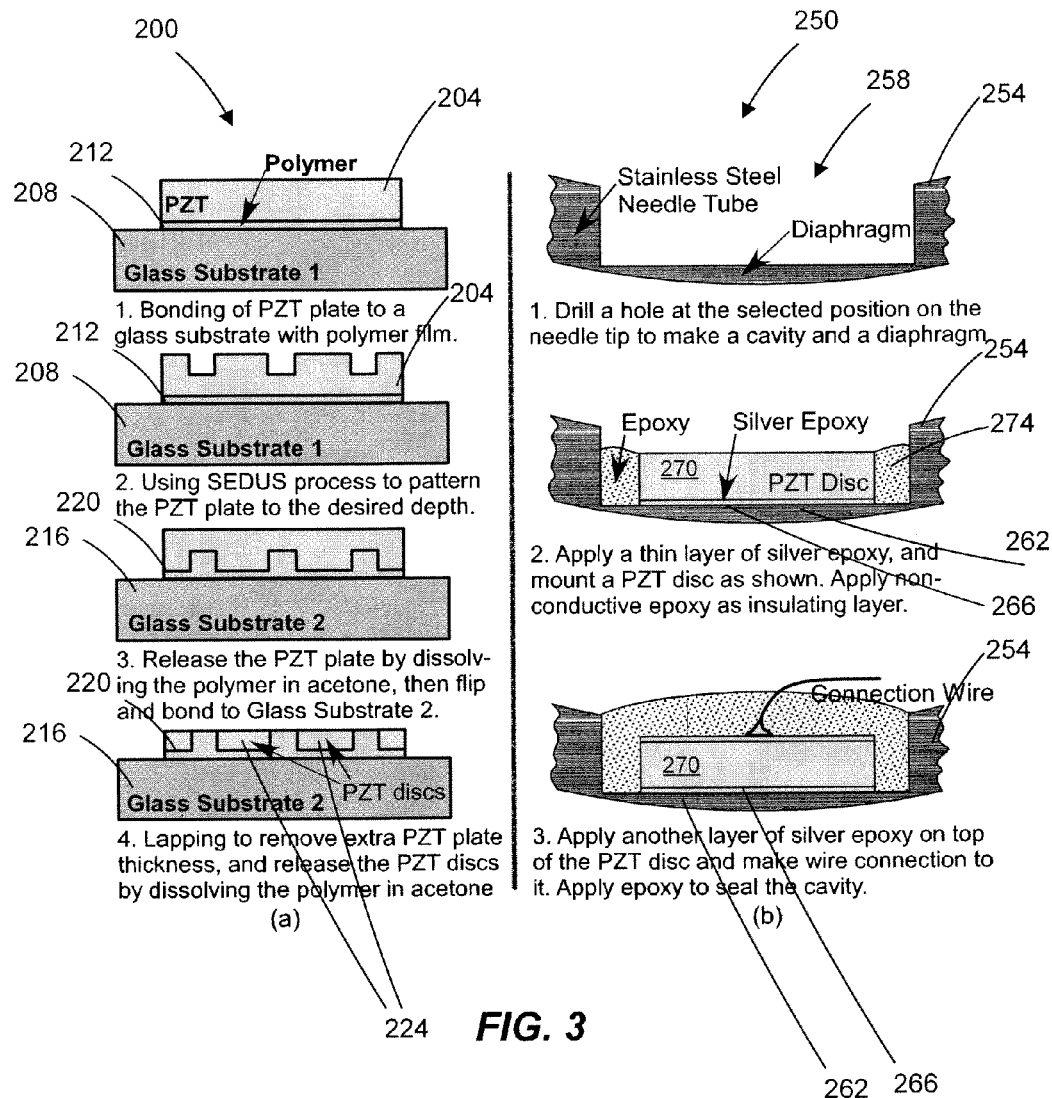
FIG. 3(a) is a diagram illustrating fabrication of the PZT sensor disk.
FIG. 3(b) is a diagram illustrating mounting of a PZT sensor disk mounted on a needle.

An example fabrication process 200 for the PZT disc 144 is shown in FIG. 3(a.) A bulk PZT-5H plate 204, which has superior material properties for sensor applications, was bonded to a glass substrate 208 by a polymer 212. Two alternative manufacturing techniques. LEEDUS and SEDUS, may be utilized during the PZT disc fabrication process was carried out to transfer a disc-array pattern onto the PZT plate. The SEDUS process is described in Li, et al., "A die-scale micromachining process for bulk PZT and its application to in-plane actuators," *Proc. IEEE MEMS* 2005, pp. 387-390 (January 2005). The LEEDUS process is described in Li, et al., "LEEDUS: A micromachining process for die-scale pattern transfer in ceramics with high resolution and throughput", *Tech. Digest Hilton Head, pp.* 324-327 (June 2004). See also, T. Li and Y. B. Gianchandani, "A micromachining process for die-scale pattern transfer in ceramics and its application to bulk piezoelectric actuators," *IEEE/ASME Microelectromechanical Systems,* 15(3), pp. 605-612, June 2006.

In the example process 200, SEDUS is utilized to pattern the PZT plate 204 to a desired depth. Then, the PZT plate 204 is released by dissolving the polymer in acetone, for example. Then, the PZT plate 204 is flipped and bonded to a glass substrate 216 by a polymer 220. Lapping is utilized to remove excess PAT plate thickness, resulting in a plurality of PZT disks 224. Then, the PZT disks 224 are released by dissolving the polymer in acetone, for example.

Figure 4A:
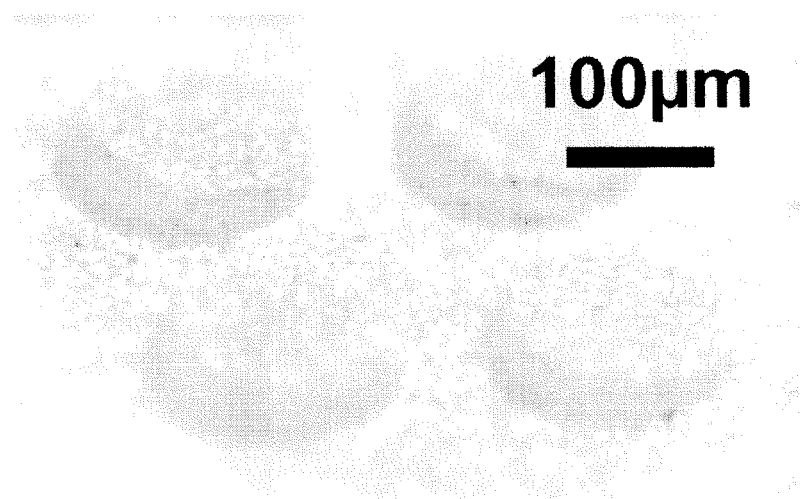
FIGS. 4(a) and 4(b) are illustrations of a PZT disks.
Figure 4B:
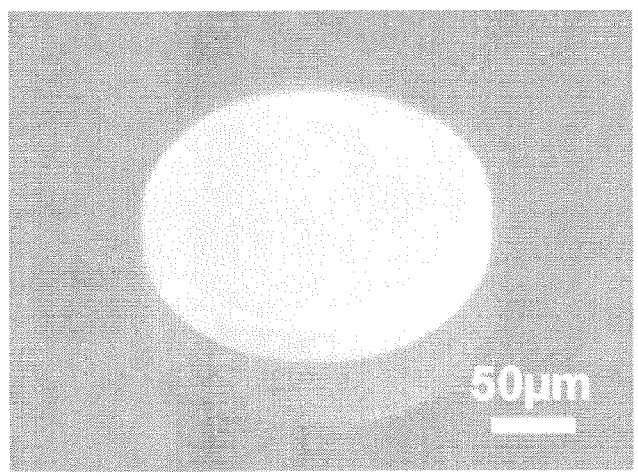

Each of the LEEDUS and SEDUS processes is a batch-mode micromachining process that uses ultrasonic machining with the help of electro-discharge machined steel tools. FIG. 4 illustrates devices formed by such a process. The discs illustrated in FIG. 4 each have a diameter of approximately 200 μm and thickness of approximately 50 μm.

Figure 5A:
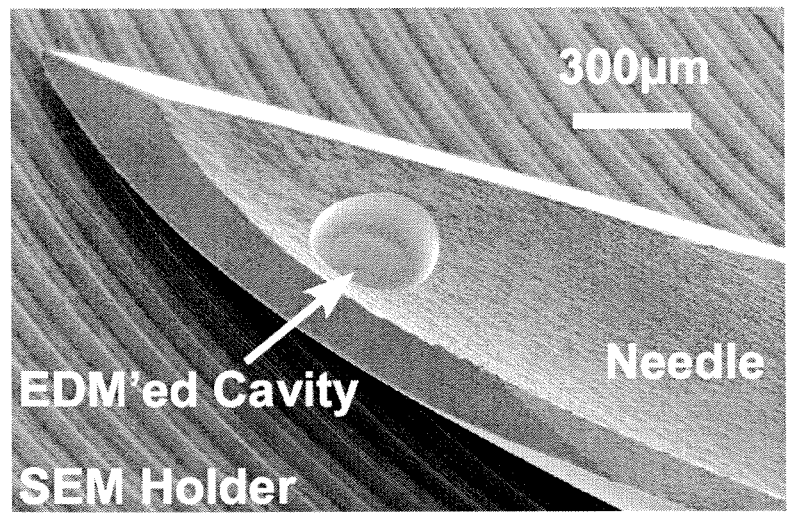
FIGS. 5(a) and 5(b) are illustrations of a tip of a biopsy needle.
Figure 5B:
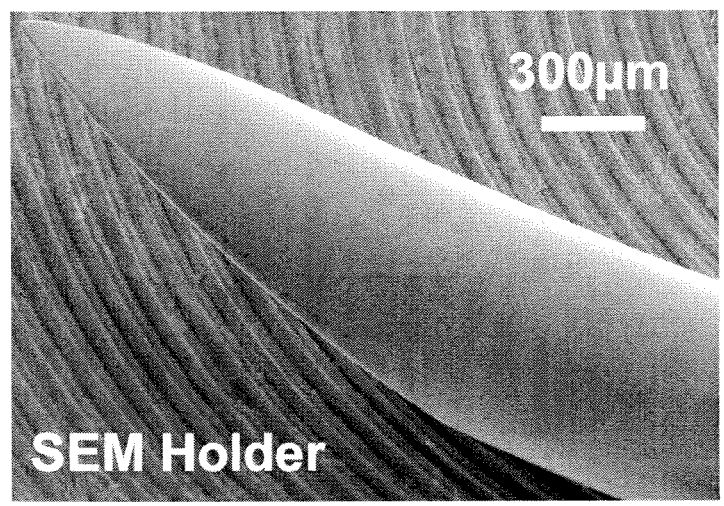
Figure 6A:
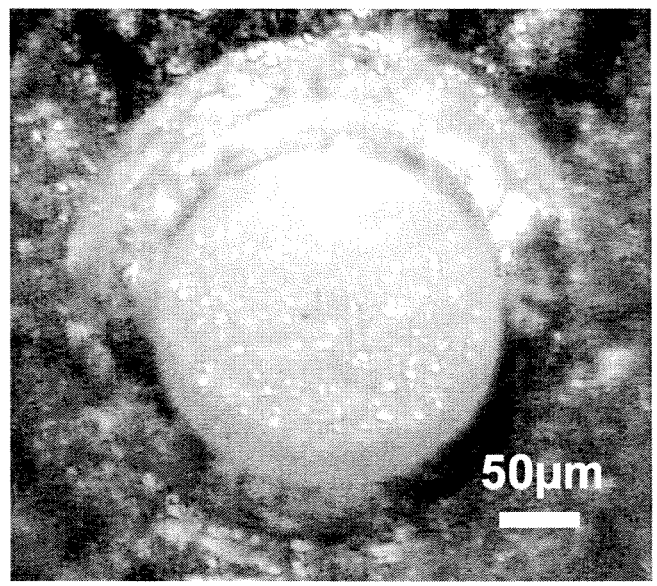
FIGS. 6(a) and 6(b) are illustrations of a tip of a biopsy needle having a PZT sensor disk mounted thereon.
Figure 6B:
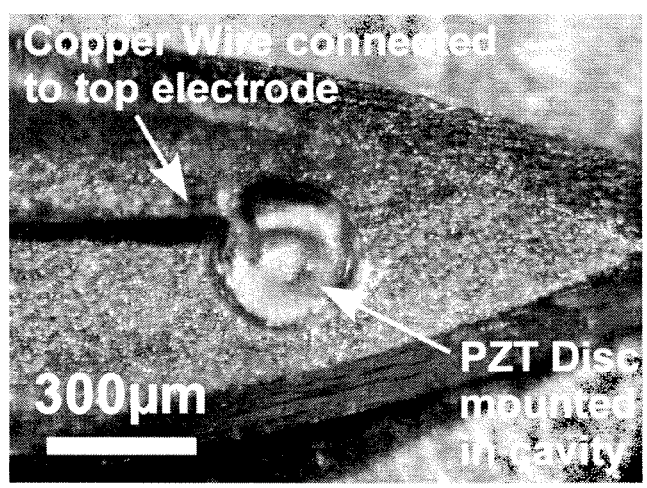

Referring to FIG. 3(b), the interior apex of the biopsy needle 254 may be machined by electro-discharge machining, for example, to form a cavity 258, in which a PZT sensor may be integrated. The cavity diameter and depth are approximately 300 μm and 150 μm, respectively. This results in a diaphragm 262 with varying thickness of 10-36 μm on the 20-gauge needle. A thin layer of silver conductive epoxy 266 was used to attach the PZT disc 270 to the bottom of the cavity 258, and another thin layer of silver conductive epoxy 278 was used to attach the lead wire 282 to the top surface of the disc 270. Non-conductive epoxy 274 was used as insulating layer and sealing material. FIG. 5 shows the micromachined cavity before sensor placement, whereas FIG. 6 shows the finished device.

For needles of smaller gauge that are sometimes needed in biopsy procedures, the wall thickness of the needle tube reduces, while the curvature of the wall increases, requiring the size of the PZT disc to be scaled down accordingly. For example, a 27-gauge needle has an outer diameter of only 406 μm and wall thickness of 102 μm. The LEEDUS/SEDUS process that has been used to fabricate the discs has the capability of handling feature size as small as 25 μm and can provide PZT elements much smaller than the current 200 μm diameter. Of course, other processes can be used as well.

Figure 7:
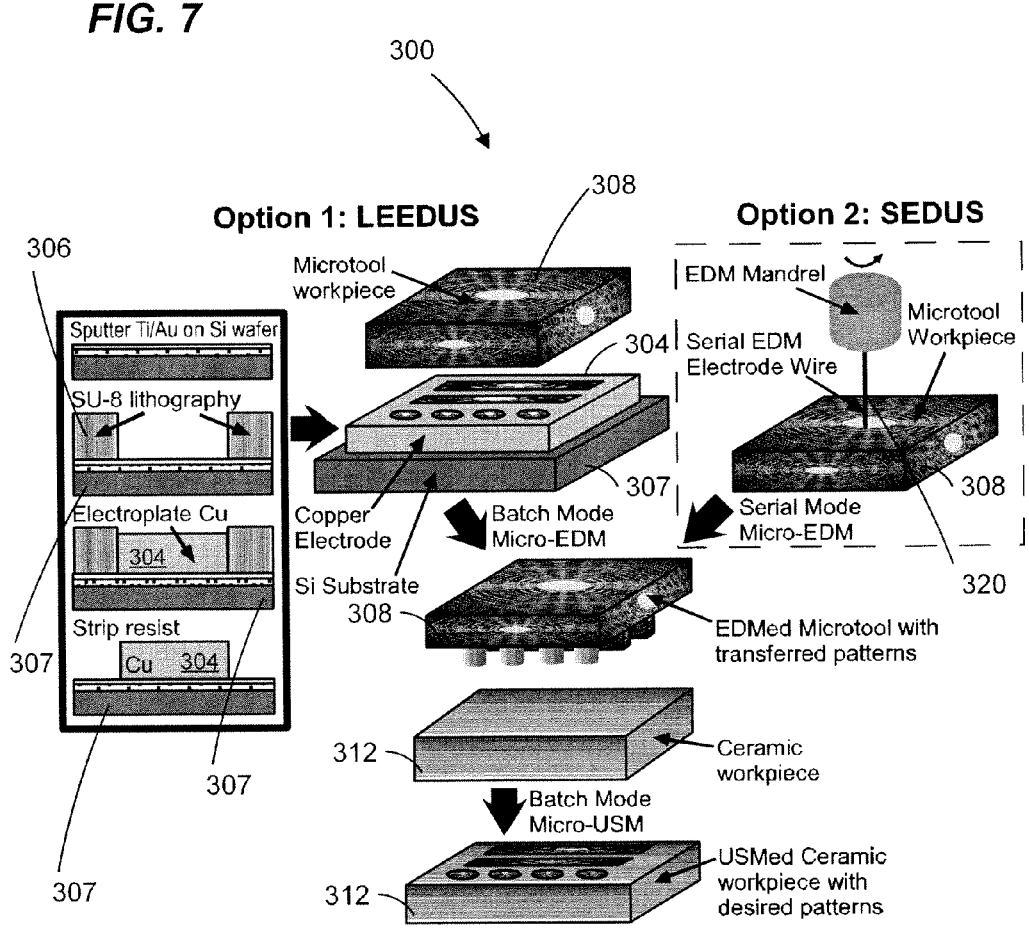
FIG. 7 is a diagram illustrating an example process for fabricating a PZT disc.

An example LEEDUS process flow is illustrated in FIG. 7. A copper structure 304 is electroplated into an SU-8 mold 306 on a silicon substrate 307 using a lithographically defined image of the final pattern. An alternative for this step is the LIGA (Lithografie, Galvanoformung, Abformung (English: Lithography, Electroplating, and Molding)) process, which has the capability of mass production of ultra fine patterned high-aspect-ratio micro structures with very smooth sidewall surfaces, and may be appropriate to fabricate the copper pattern 304 when an aspect ratio greater than 10:1 is desired. The copper pattern 304 on the silicon die 307 is then used as an electrode to perform batch mode micro electrical discharge machining (μEDM) on a hard-metal microtool workpiece 308, transferring the corresponding negative die-scale pattern onto it. During the machining, electric discharges are fired between the electrode 304 and the workpiece 308 when they are both immersed in dielectric oil. This wears away both of them, but the workpiece 308 is eroded much faster. By using lithographically defined electrodes, the batch mode μEDM may provide high throughput, high density and high uniformity over the whole array on any conductive materials. Finally the microtool 308 is mounted on an ultrasonic machining setup for batch mode micro ultrasonic machining (μUSM) of a ceramic workpiece 312, thus having the desired positive pattern transferred onto it. Non-lithographic rapid-prototyping can also be performed for simple patterns by a similar process, in which the original serial μEDM function of the μEDM machine is used to define the pattern on the microtool by running a program on a computer to control the "writing" movement of the rotating EDM electrode wire 320 on the microtool workpiece 308. This derivative of the process is called SEDUS (serial electro-discharge and ultrasonic machining).

Figure 8:
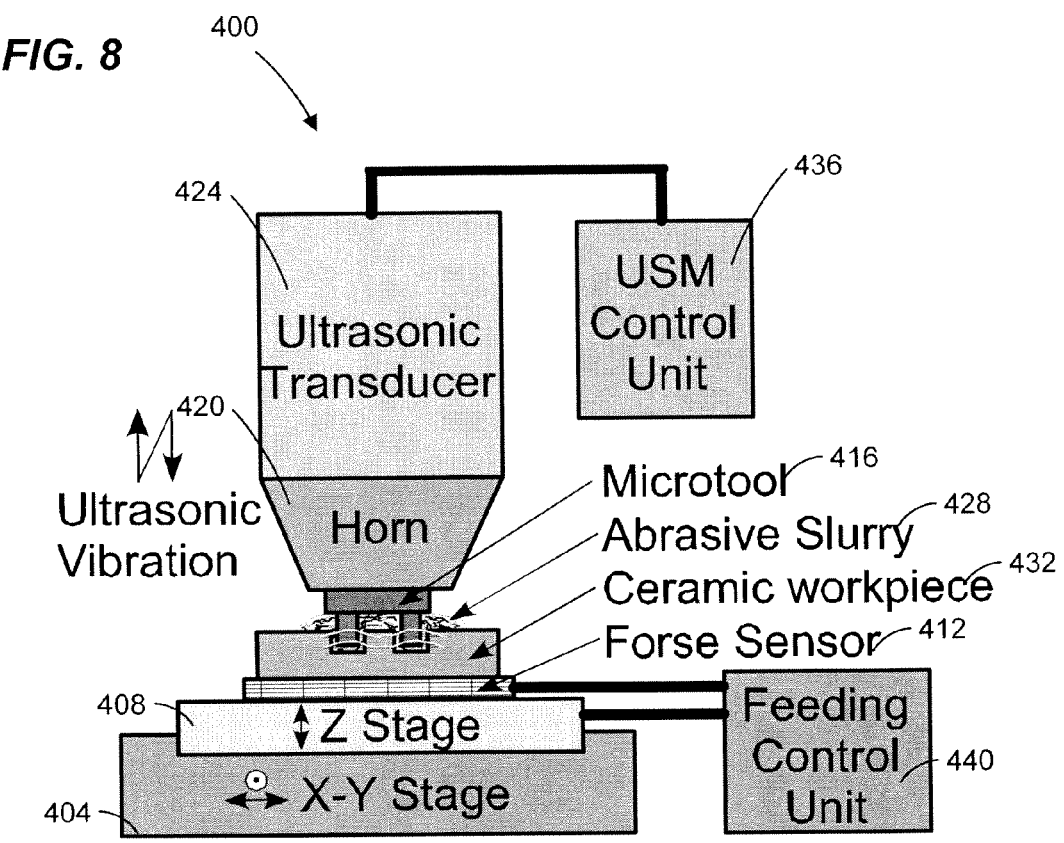
FIG. 8 is a diagram of an example setup for batch mode processing of PZT discs.

A diagram for an example setup 400 built for batch mode μUSM is shown in FIG. 8. This example setup 400 has a manually controlled X-Y stage 404 for relative positioning of the microtool 416 and the ceramic workpiece 432. The Z stage 408 is motorized and computer-controllable. A force sensor 412 is implemented on the Z stage 408 to monitor the machining load and provide feedback signal when necessary, so that the setup 400 can work in either a constant machining load mode or a constant feeding speed mode. The vibration amplitude of the ultrasonic transducer 424 is adjustable down to 20% of the full scale output. The micro electrical discharge machined microtool 416 is mounted by epoxy at the tip of the horn 420 where the vibration energy generated by the ultrasonic transducer 424 is maximized in the vertical direction. Abrasive slurry 428 which consists of water and fine abrasive powders is supplied between the tip of the microtool 416 and a ceramic workpiece 432. The vibrating tip of the microtool 416 is fed into the ceramic workpiece 432. The ultrasonic motion of the microtool 416 imparts velocity to the abrasive particles on its downward stroke. These particles, in turn, are responsible for the erosion of the workpiece 432, thus creating the desired cavities in the shape of the microtool 416.

A variety of alternative manufacturing techniques may be used to fabricate the disclosed devices. For instance, powder blasting, milling, drilling and scribing may be alternatively or additionally be employed, among other alternatives, such as laser machining.

Figure 9A:
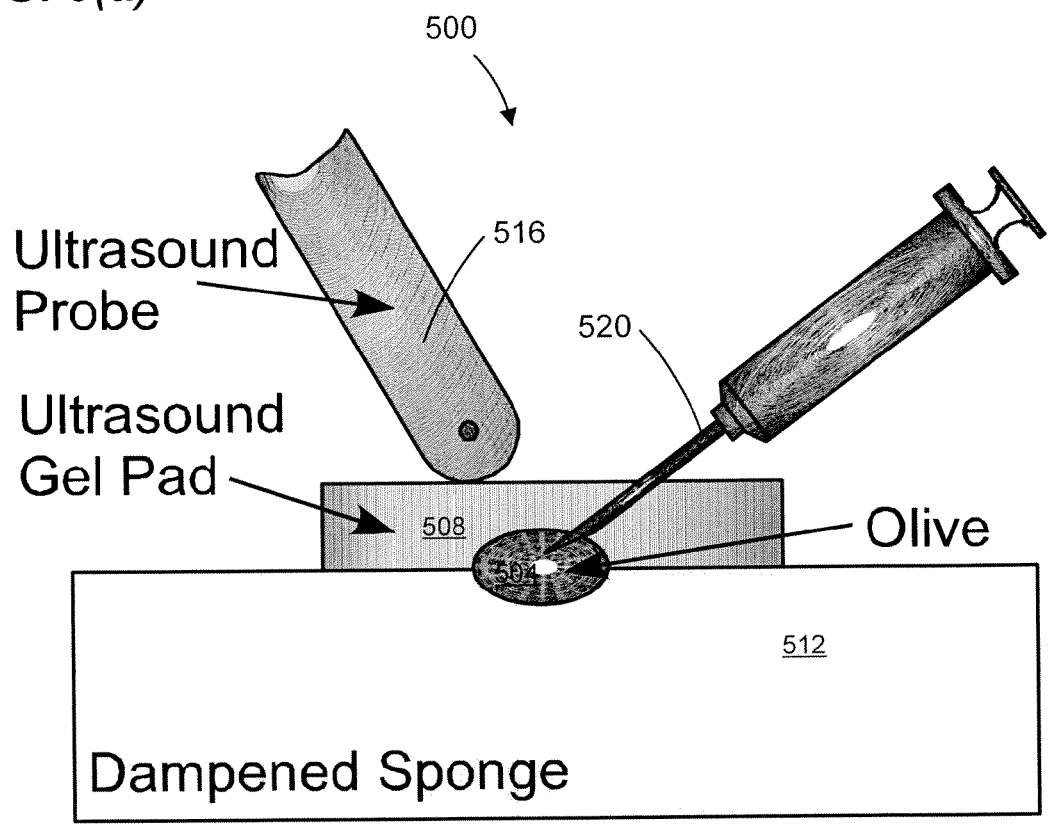
FIG. 9(a) is a diagram illustrating a procedure used for physician training in thyroid FNA biopsy.
Figure 9B:
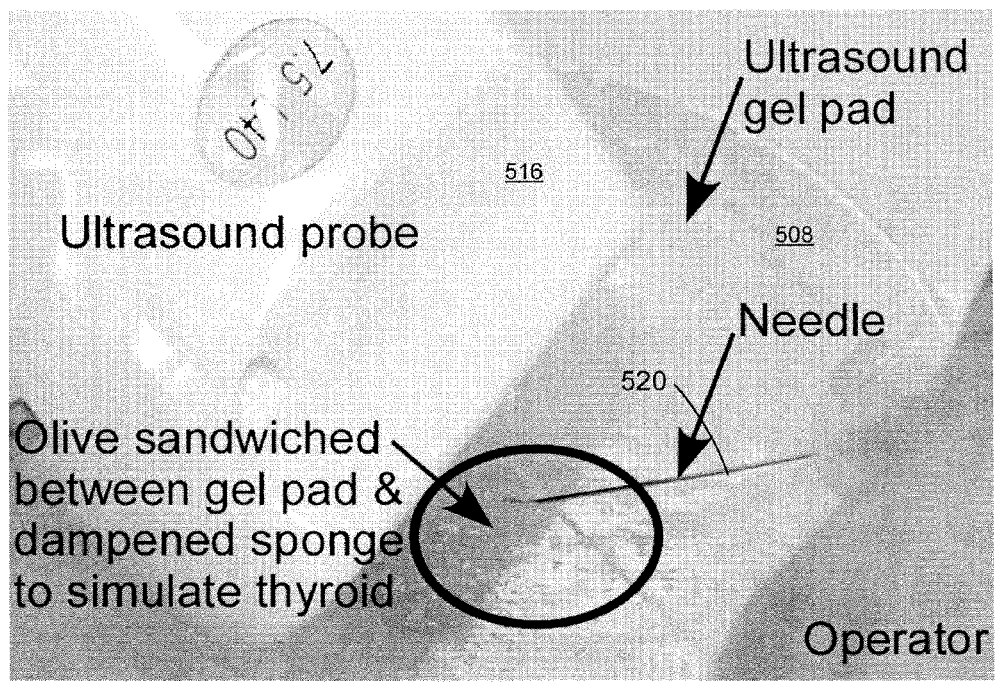
FIG. 9(b) is a picture of the procedure of FIG. 9(a)
Figure 9C:
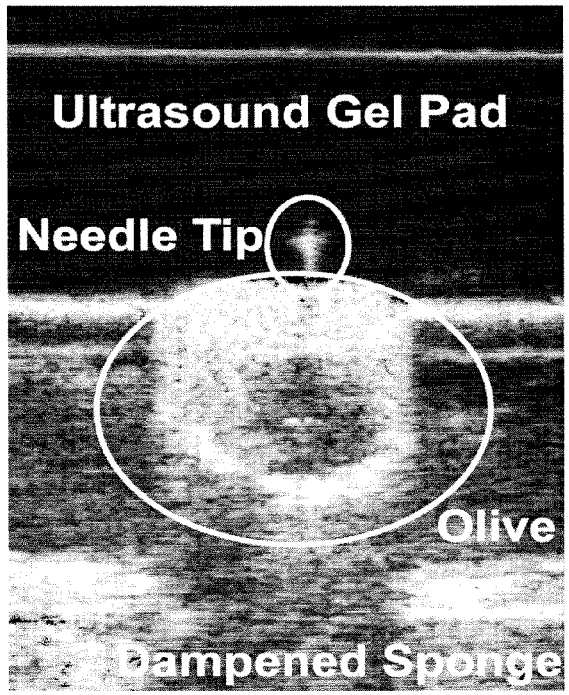
FIG. 9(c) is an ultrasound image of a needle used in the procedure of FIG. 9(a)

FIG. 9(a) is a diagram illustrating a procedure used for physician training in thyroid FNA biopsy: a pickled olive 504 simulates the thyroid nodule, while an Aquaflex® ultrasound gel pad 508 (Model 04-02 from Parker Labs Inc.) and dampened sponge 512 simulate the surrounding tissues. A trainee holds the ultrasound probe 516 with one hand and inserts the needle 520 into the target region (FIG. 9(b)), while observing its position using a real-time 2D ultrasound image (FIG. 9(c)).

The fabricated devices were tested by penetrating the biopsy needle 520 into the following: (A) the physician training arrangement of FIG. 9(a); and (B) porcine tissue consisting of fat and muscle layers. An HP4195 spectrum analyzer was used to obtain impedance spectra.

Figure 10A:
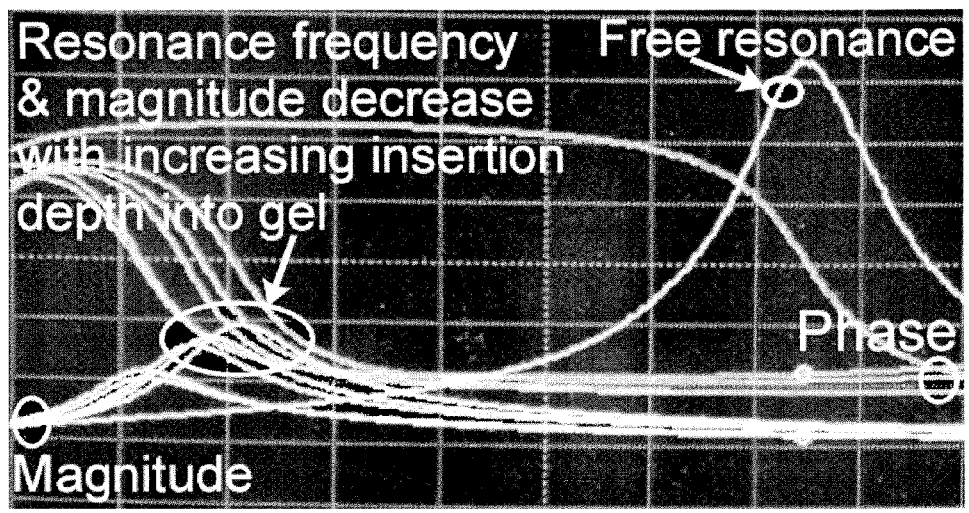
FIGS. 10(a) and 10(b) are graphs showing results of an experiment.
Figure 10B:
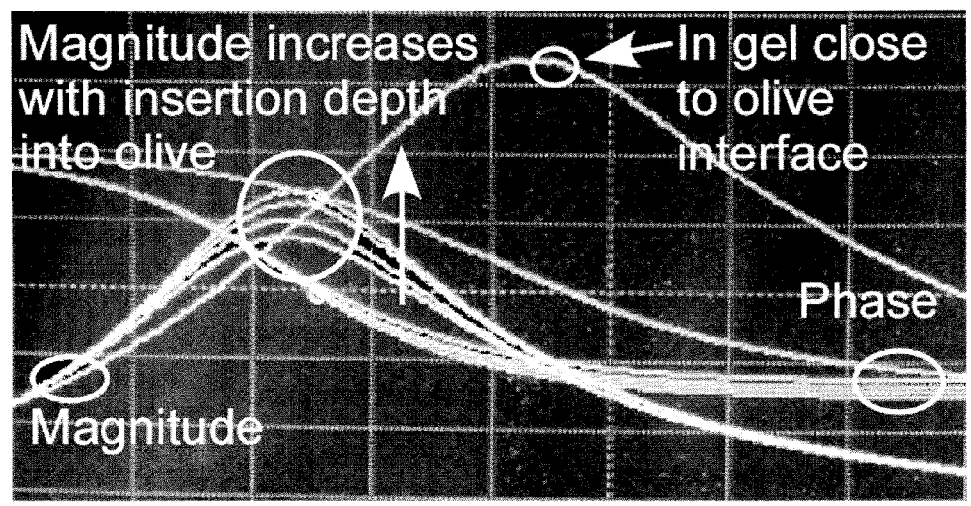
Figure 11:
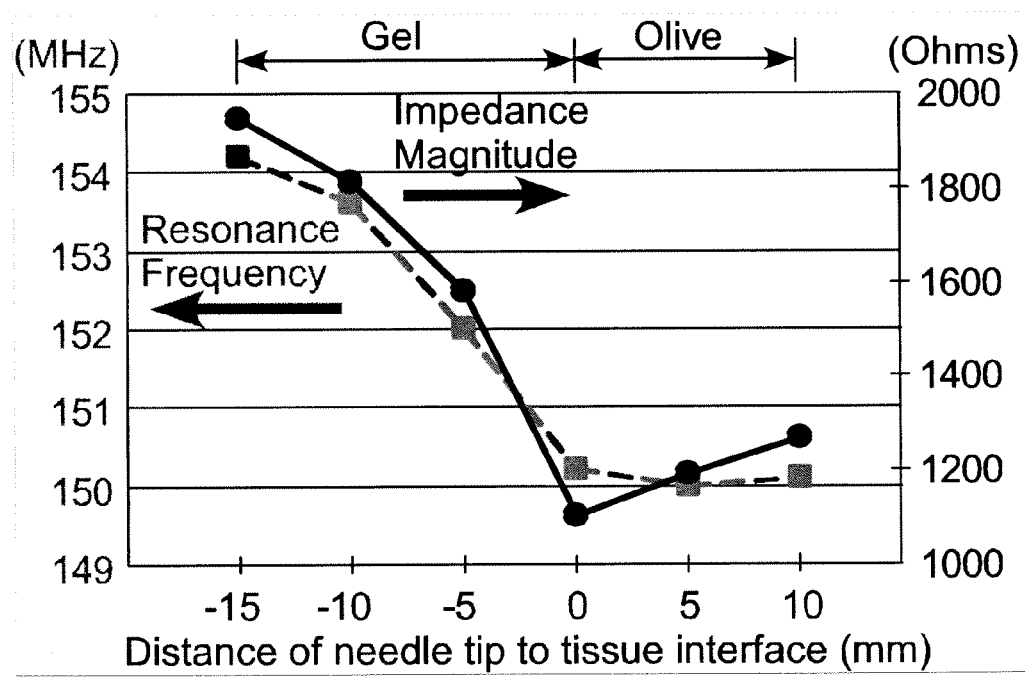
FIG. 11 is a graph showing results of an experiment.

The results of test A are shown in FIGS. 10(a), 10(b) and 11. A resonance mode with a relatively high frequency and large Q was selected for testing. When the needle was inserted from free space into the ultrasound gel pad, the resonance frequency dropped from 176 MHz to 154 MHz. Both the resonance frequency and the peak impedance decreased gradually with advancement of the needle into the gel pad. After the needle tip reached the olive, the resonance frequency stayed almost constant while the impedance peak magnitude started increasing with injecting depth into the olive. The electrical characteristics are thereby indicative of a tissue contrast between the olive and the surrounding sponge, which emulate the contrast between the thyroid nodule and the surrounding tissues.

Figure 12A:
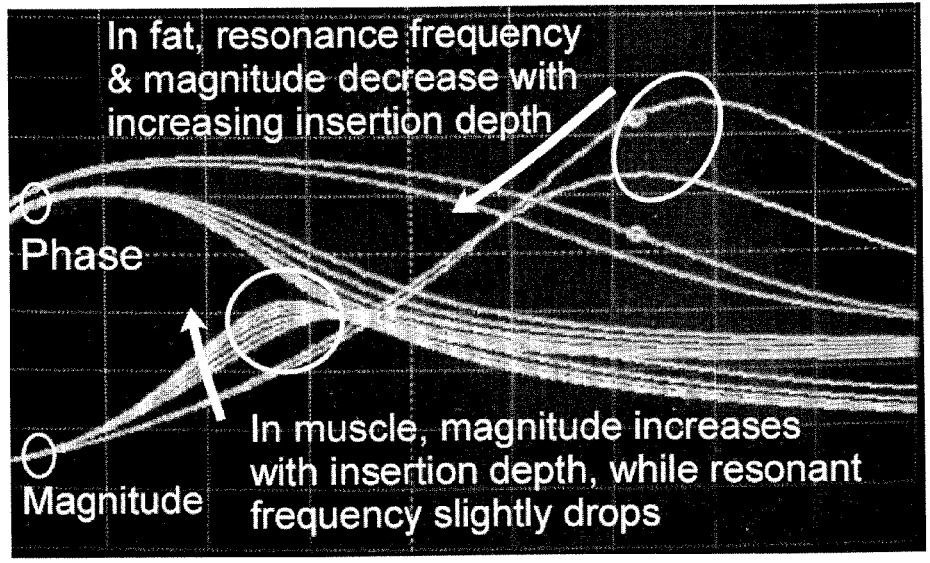
FIGS. 12(a) and 12(b) are graphs showing results of an experiment.
Figure 12B:
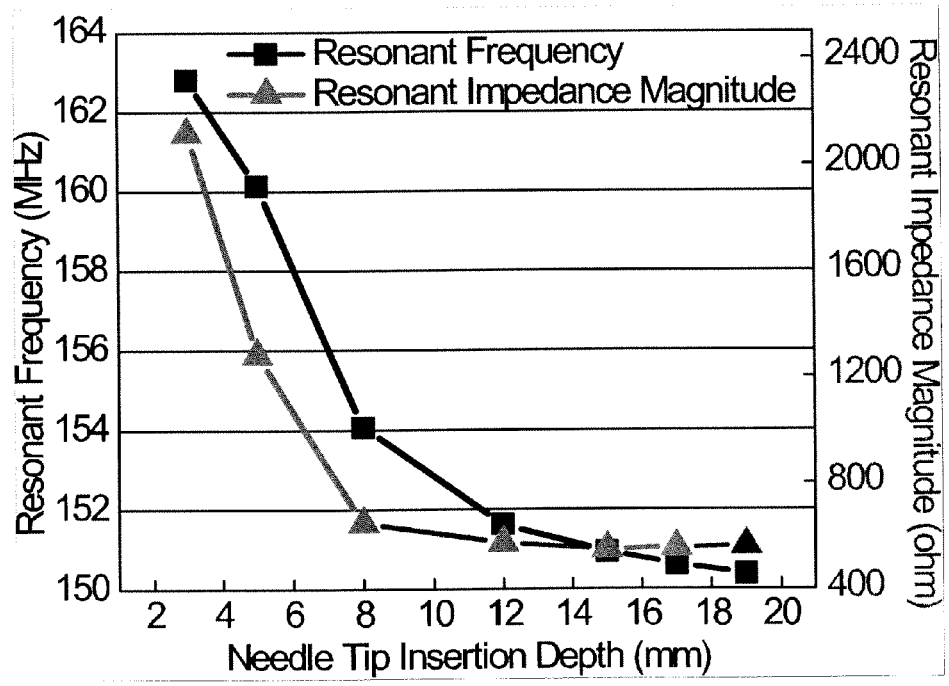

The results of test B are shown in FIGS. 12(a) and 12(b). Both the resonance frequency and the impedance peak magnitude gradually decrease as the needle is inserted into the fatty tissue. Once the needle tip moves into the muscle, the impedance peak magnitude starts to increase slightly, while the resonance frequency further drops with a much smaller slope (≈⅕ of that in fat).

Figure 13:
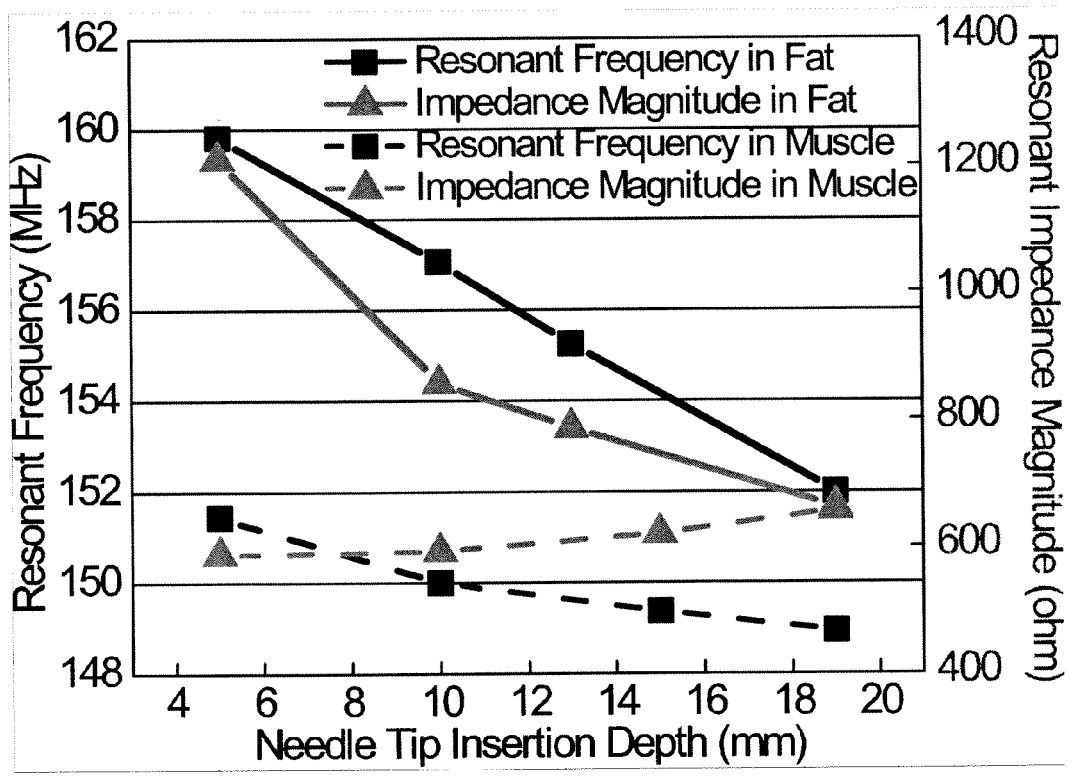
FIG. 13 is a graph showing results of an experiment.

The porcine fat is not optically transparent like the ultrasound gel pad, making visual observation of the needle position more difficult for test B. Two additional tests were then carried out to individually study the response of the sensor to porcine fat or muscle by inserting the needle directly from free space into each kind of tissue. As shown in FIG. 13, impedance characteristics similar to that in FIGS. 12(a) and 12(b) were observed in each case. This confirms that the electrical characteristics shown in FIGS. 12(a) and 12(b) demonstrated the tissue contrast between animal fat and muscle.

A PZT disc that is actuated in longitudinal mode for free vibration in the direction of its thickness has both the piezoelectric polarization and the applied electrical field parallel to its thickness. Mechanical resonance for such a disc occurs when its thickness $t_0$ equals the odd multiples of half of the vibration wavelength, $\lambda/2$, or equivalently when $$f_{(n)} = \frac{n \cdot v_0}{2t_0}, \quad (1)$$

$$n = 1, 3, 5\ldots$$

where $f_{(n)}$ is the $n^{th}$ resonance frequency, $v_0 = \lambda \cdot f_{(n)}$ is the vibration velocity in the material, and n is a positive integer that represents the harmonic number. Due to the piezoelectric effect of the disc, these mechanical resonances correspond to a series of electrical impedance peaks of the PZT disc, and the mechanical resonance frequency, $f_{(n)}$, is equal to the antiresonance frequency, $f_{a(n)}$, of the electrical impedance for the disc in this thickness longitudinal driving mode (also referred to as maximum impedance frequency $f_m$). The thickness of the PZT disc $t_0$ will thus determine the location of the impedance peaks on the spectra, and diameter R of the disc should be several times larger than $t_0$ in order to reduce the cross coupling from lateral wave resonance mode by reducing the lateral resonance frequency. When the mechanical boundary conditions, such as mass and elastic loading, are changed by contact with the materials to be tested, the mechanical resonance of the PZT disc will change accordingly. This is transduced into changes in the electrical impedance peaks of the PZT disc, and can be monitored by measuring the electrical impedance spectra.

Figure 14:
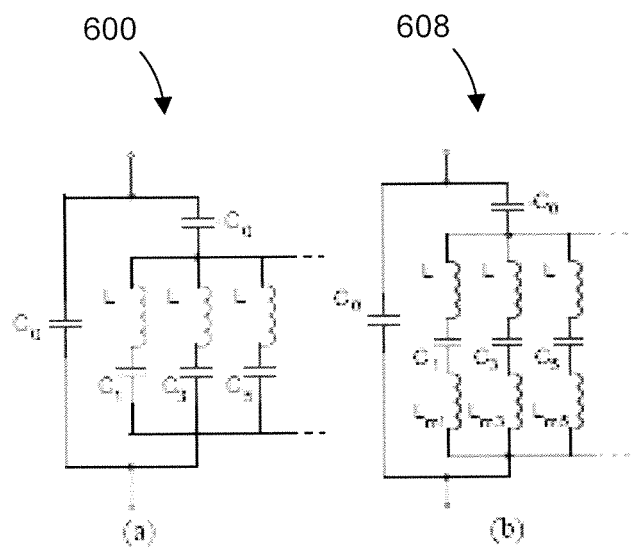
FIG. 14(a) is a circuit diagram of a BVD equivalent circuit of a piezoelectric resonator.
FIG. 14(b) is a circuit diagram of a modified BVD equivalent circuit of a piezoelectric resonator.

A lumped-element Butterworth-Van Dyke (BVD) equivalent circuit can be used to model the electrical characteristics of the PZT disc in the absence of loading. FIG. 14(a) is a circuit diagram of a BVD equivalent circuit 600 of a piezoelectric resonator in longitudinal vibration mode with loss mechanism ignored. A modification to this original BVD circuit accommodates the loading effect as shown in the circuit 608 of FIG. 14(b): inductors $L_{m(n)}$ are used to model mass loading, such as a diaphragm attached to a piezoelectric sensor. The clamped capacitance between the two electrodes of the disc is denoted $C_0$, and an infinite number of series $LC_n$ (n=1, 3, 5 . . . ) motional branches are connected in parallel. The first branch of L and $C_1$ corresponds to the fundamental resonance mode, and the $n^{th}$ branch of L and $C_n$ represents the $n^{th}$ mode defined by Equation (1). The $n^{th}$ antiresonance frequency $f_{a(n)}$ and resonance frequency $f_{r(n)}$ of the measured electrical impedance for the original BVD circuit without loading inductance $L_{m(n)}$ are:

$$f_{a(n)} = f_{(n)} = \frac{1}{2\pi\sqrt{LC_n}}, \quad (2)$$

$$n = 1, 3, 5\ldots$$

$$f_{r(n)} = \frac{1}{2\pi\sqrt{LC_n \frac{C_0}{C_0 - C_n}}}, \quad (3)$$

$$n = 1, 3, 5\ldots$$

The circuit elements are related to the physical parameters of the PZT disc by:

$$C_0 = \frac{\varepsilon \cdot A}{t_0} \quad (4)$$

$$C_n = \frac{8k_t^2}{n^2\pi^2}C_0, \quad (5)$$

$$n = 1, 3, 5\ldots$$

$$L = \frac{1}{4\pi^2 f_{a1}^2 C_1} \quad (6)$$

$$R = \frac{\eta_0}{\rho_0 v_0^2 C_1}\left(\frac{f}{f_{a1}}\right), \quad (7)$$

$$n = 1, 3, 5\ldots$$

where $\in$ is the permittivity of the piezoelectric layer; A and $t_0$ are the area and thickness of the PZT disc, respectively; $k_t^2$ is the electromechanical coupling constant determined by material properties including piezoelectric constant, stiffness, and permittivity of the piezoelectric material; $v_0$ and $\eta_0$ are the acoustic velocity and viscosity of the piezoelectric layer, respectively; and $\rho_0$ is the density of the piezoelectric layer. As shown in Equations (2) and (3), both $f_{a(n)}$ and $f_{r(n)}$ are related to motional parameters L and $C_n$ which are coupled with mechanical boundary conditions, so either one can be used to monitor the resonance change. However, the antiresonance modes, $f_{a(n)}$, are preferred for this longitudinal piezoelectric coupling because it is fundamentally related only to the thickness of the disc, and less affected by circuit parameters such as variation of $C_0$ due to parasitic capacitances.

The inductors $L_{m(n)}$ that represent loading, are related to the physical parameters of the PZT disc and the added mass by $$L_{m(n)} = \frac{4 f_{a1} L \rho_m t_m}{n \rho_0 v_0}, \quad (8)$$

$$n = 1, 3, 5\ldots$$

where $\rho_m$ and $t_m$ are the density and thickness of the added mass layer, respectively. The thickness, $t_m$, should be as small as possible, since it is inversely proportional to the sensitivity of the sensor to any additional mass loading on the diaphragm.

Figure 15:
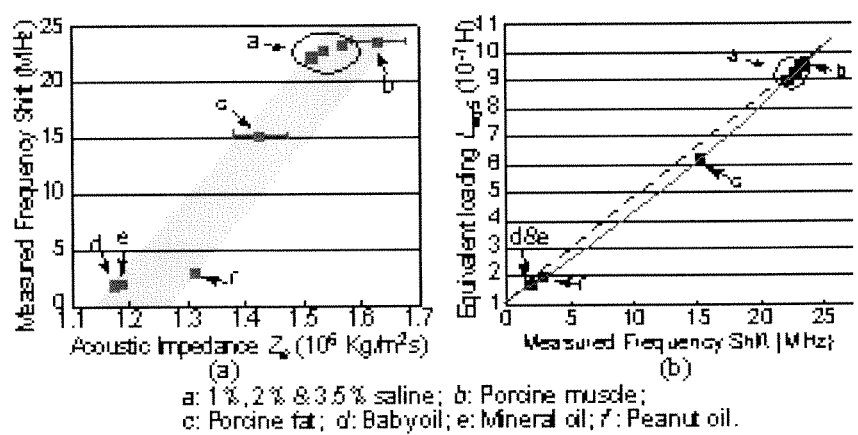
FIG. 15(a) and FIG. 15(b) are graphs of measured values associated with a piezoelectric sensor.

The resonance shift ($\Delta f$) of the piezoelectric sensor is dependent on both the mass loading effect and elastic properties of the samples. The $Z_a$ of a sample is the product of its density and acoustic velocity, the latter being further related to the elastic bulk modulus of the material. Thus, an empirical tissue contrast model can be built for the biopsy device by plotting the measured $\Delta f$ versus $Z_a$ as shown in FIGS. 15(a) and 15(b). The relationship is approximately proportional, as shown in the shaded area, considering the uncertainty in the acoustic properties of the samples. The data used in this plot are from Table 1.

To include the tissue loading effect in the model, $L_{m(n)}$ can be extended by adding series another equivalent loading inductance $L_{eq(n)}$. This additional inductance is an equivalent that includes the effect of both mass and elastic loading for modeling convenience. The frequency of each harmonic mode $f_{(n)}$, or equivalently the frequency of each electrical impedance peak can then be denoted as:

$$f_{a(n)} = \frac{1}{2\pi\sqrt{(L + L_{m(n)} + L_{eq(n)})C_n}}, \quad (9)$$

$$n = 1, 3, 5\ldots$$

In experiments, the $5^{th}$ harmonic mode (at 176 MHz in air) was found to have a higher Q than the fundamental and $3^{rd}$ harmonic mode, and was consequently selected for measurement. This is possibly due to less acoustic energy loss in the $5^{th}$ harmonic mode than in the $1^{st}$ and $3^{rd}$ modes, but may be due to other reasons additionally or alternatively. In these experiments, the $3^{rd}$ $RLC_n$ branch (for the $5^{th}$ harmonic mode) of the modified BVD circuit was of most interest. The calculated equivalent loading $L_{eq5}$ for each of the samples used to build the empirical tissue contrast model is listed in Table 1 and plotted as a function of the measured frequency shift $\Delta f_{a5}$ in FIG. 15(b). The two plots in FIGS. 15(a) and 15(b) provide an example empirical tissue contrast model (i.e., the relationship of $Z_a$ to $\Delta f_{a5}$) and the relationship of $L_{eq5}$ to $\Delta f_{a5}$. These relationships, along with the modified BVD circuit model, may be useful for relating physical parameters of the device and samples to $\Delta f$ for design and optimization of a sensor.

Figure 16:
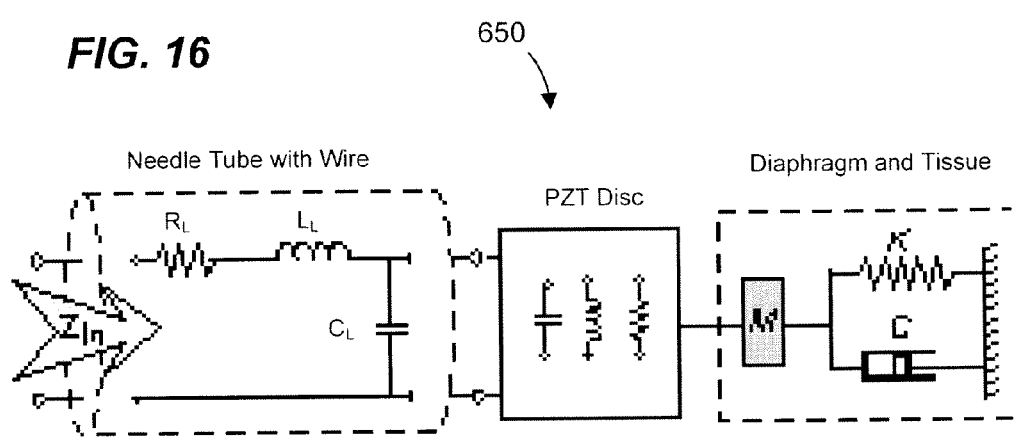
FIG. 16 is a diagram of an equivalent circuit model of a biopsy device.

Transmission line characteristics of a stainless steel needle tube along with an inside copper wire may be worth considering because they may affect the measured electrical impedance. In the absence of a liquid within the biopsy needle, i.e. while the needle is approaching the target, the connection wire to the sensor and the surrounding needle structure can be approximately modeled as a coaxial line. An equivalent circuit model 605 is shown in FIG. 16. In this model, the PZT disc can be replaced with an equivalent static capacitor for the transmission line analysis, no the piezoelectric effect is not considered. In this analysis, the extension wire that connects the needle tube to the impedance analyzer is neglected because it can be compensated during a measurement. According to the classic transmission line theory for a terminated lossy coaxial line, the input impedance $Z_{in}$ is $$Z_{in} = Z_0 \frac{Z_P + Z_0 \cdot \tanh \gamma l}{Z_0 + Z_P \cdot \tanh \gamma l} \quad (10)$$

where $Z_p$ is the impedance of the equivalent static capacitor replacing the PZT disc, and the capacitance value is 20 pF for this analysis; l is the length of the coaxial line and is equal to

TABLE 1

| | Samples | $\Delta f$ (MHz) | Density (Kg/m³) | Sound Velocity (m/s) | Acoustic Impedance $Z_a$ ($10^6$ Kg/m²s) | Equivalent Loading Inductance $L_{eq5}$ ($10^{-7}$ H) |
|---|---|---|---|---|---|---|
| a. | Saline-1% [26] | 22.2 | 1005 | 1507 | 1.515 | 8.98 |
| | Saline-2% [26] | 22.8 | 1012 | 1518 | 1.537 | 9.24 |
| | Saline-3.5% [26] | 23.3 | 1023 | 1534 | 1.570 | 9.44 |
| b. | Porcine muscle [27] | 23.6 | 1040 | 1568 | 1.630 | 9.57 |
| c. | Porcine fat [27] | 15.2 | 970 | 1470 | 1.426 | 6.14 |
| d. | Body Oil [28] | 1.9 | 821 | 1430 | 1.174 | 1.68 |
| e. | Mineral Oil [28] | 2.0 | 825 | 1440 | 1.188 | 1.71 |
| f. | Peanut Oil [28] | 2.9 | 914 | 1436 | 1.313 | 1.98 |

25 mm; $Z_0$ and $\gamma$ are the transmission line characteristic impedance and the complex propagation constant, respectively, and are both related to the transmission line parameters $R_L$, $C_L$, and $L_L$ by equations found in the classic transmission line theory. These parameters $R_L$, $C_L$, and $L_L$ are further related to the physical parameters of the coaxial line, including the radius of the copper wire $r_a$, and the inner radius of the needle tube $r_b$. Since air is used as the dielectric material for this coaxial line model, its permittivity and permeability properties are used in the analysis.

Figure 17A:
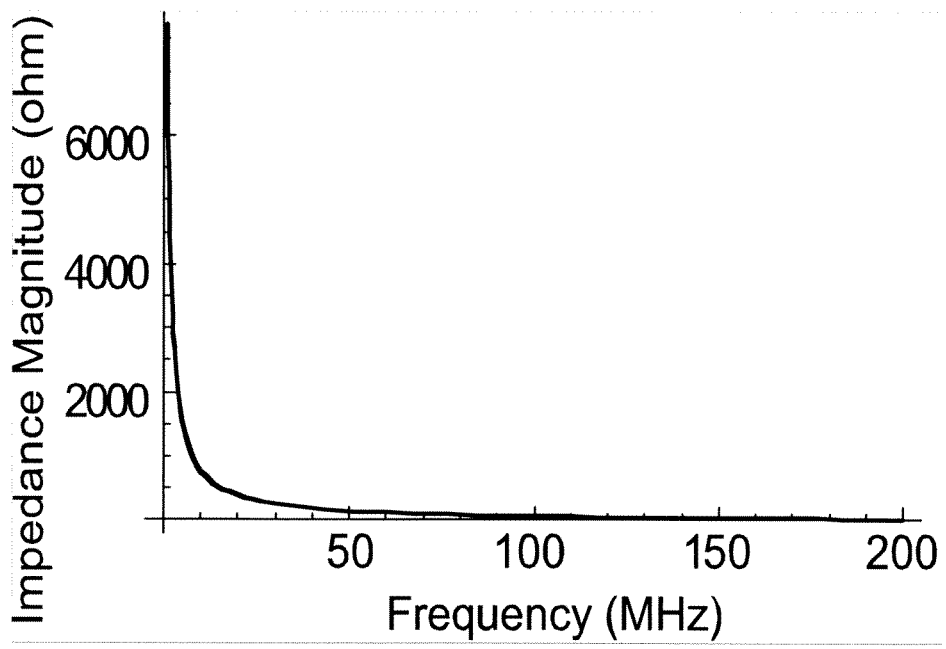
FIG. 17(a) is a graph of impedance magnitude versus frequency associated with the circuit model of FIG. 16.
Figure 17B:
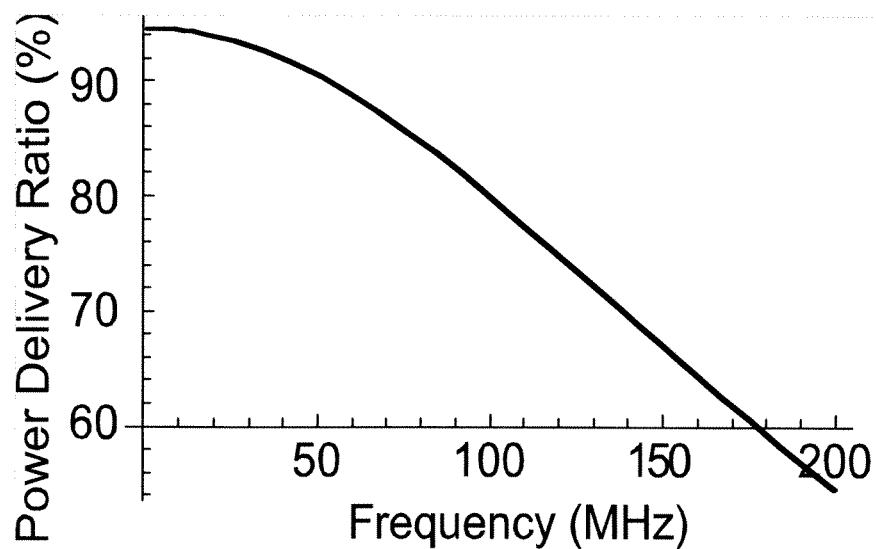
FIG. 17(b) is a graph of power delivery ratio versus frequency associated with the circuit model of FIG. 16.

According to this approximate analysis, the calculated input impedance $Z_{in}$ of this model drops smoothly within the frequency range of interest (FIG. 17(a)), and the length of the equivalent coaxial cable can be considered much shorter than the calculated transmission line characteristic wavelength. Thus, in some implementations, the effect of the needle tube can be basically ignored. In one specific implementation, the calculated ratio of power delivered to the PZT disc through the needle tube and copper wire was found to vary almost linearly with frequency from ≈95% at 1 MHz to ≈65% at 160 MHz, as seen in FIG. 17(b).

A micromachined device has been demonstrated to achieve in-situ real-time tissue contrast detection during FNA biopsy of thyroid nodules. A batch-fabricated bulk PZT sensor was implemented into a cavity that is in the wall of a needle at its apex. The device was tested in a simulated scheme for physician training, as well as in porcine tissue consisting of fat and muscle layers. The device demonstrated tissue contrast in both of the test schemes through a change in the resonance frequency and peak magnitude of the PZT electric impedance. A preliminary analysis based on a circuit model has been carried out for the tissue contrast sensor.

Figure 18:
FIG. 18 is an illustration of an experiment performed with a breast phantom.

A further example is now described in connection with an Ultra/Phonic BP Breast Phantom. The experiment target sample is the Ultra/Phonic BP Breast Phantom (FIG. 18) made by the Pharmaceutical Innovations, Inc. (http://www.pharminnovations.com). This is a reusable, self-healing solid gel breast phantom. It is used for hand/eye coordination practice with ultrasound guided needle biopsy, providing simulated clinical experience for breast biopsies with randomly embedded target structures of various size and density. The palpable targets are acoustically accurate.

Figure 19:
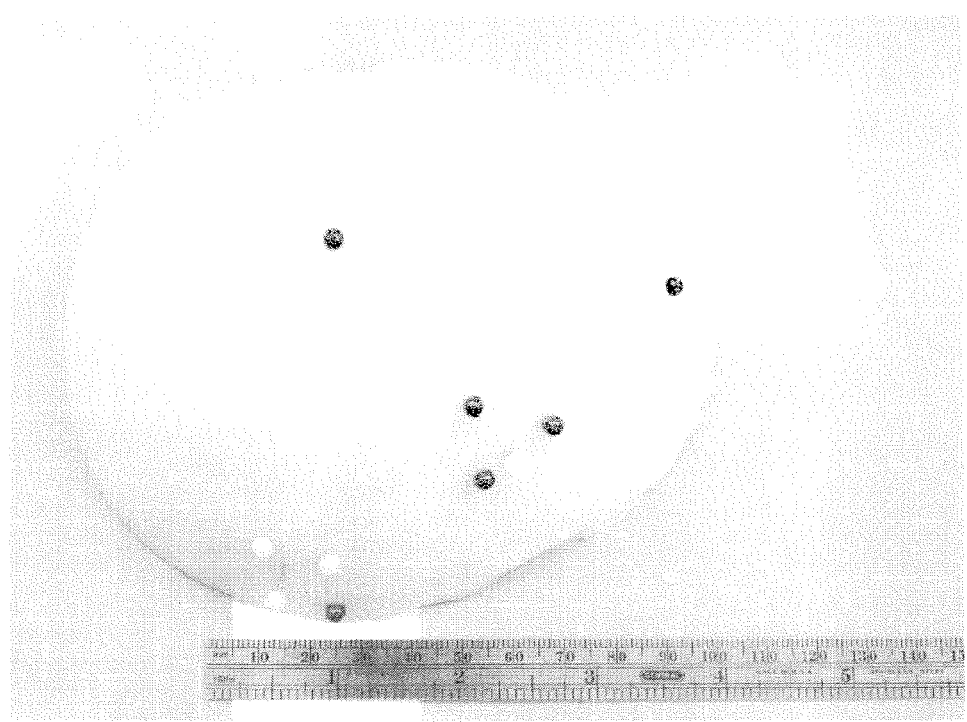
FIG. 19 is an illustration of the breast phantom experiment.
Figure 20A:
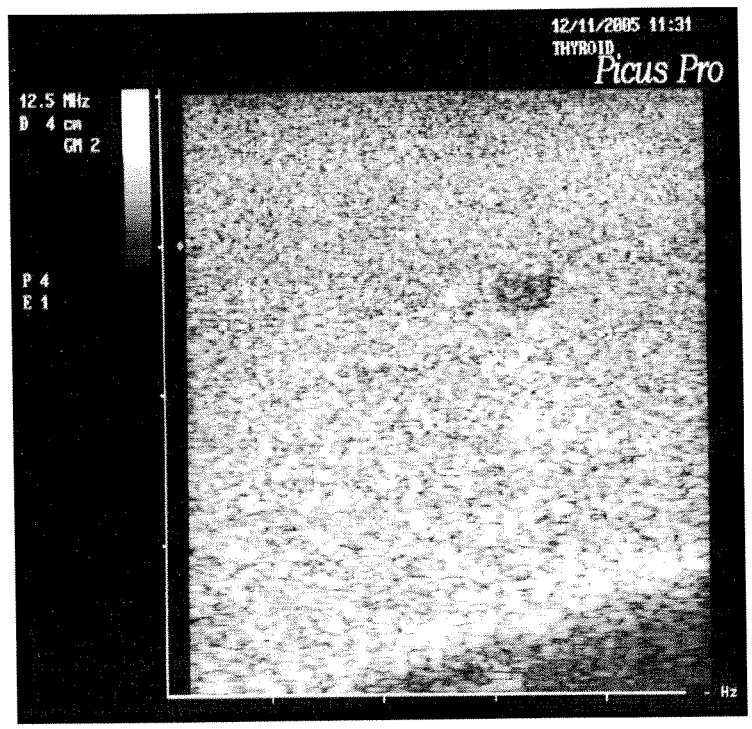
FIGS. 20(a) and 20(b) are ultrasound images of the breast phantom experiment.

The following experiment first uses a medical ultrasound machine to locate the targets. The nodule targets in the breast phantom are randomly distributed and not easily palpable. To prepare the breast phantom sample for a biopsy tool experiment, a medical ultrasound machine was used to find the location of these randomly distributed nodule targets within the phantom. As the usable length of the biopsy tool needle is limited to ~25 mm, two nodules within the depth of 15 mm from the phantom surface were located as shown in FIG. 19. Pins grouped by color were used to mark the location of the nodules, while the three red pins form an orthogonal coordinate system. The ultrasound images for the two nodules are shown in FIGS. 20(a) and 20(b).

Figure 20B:
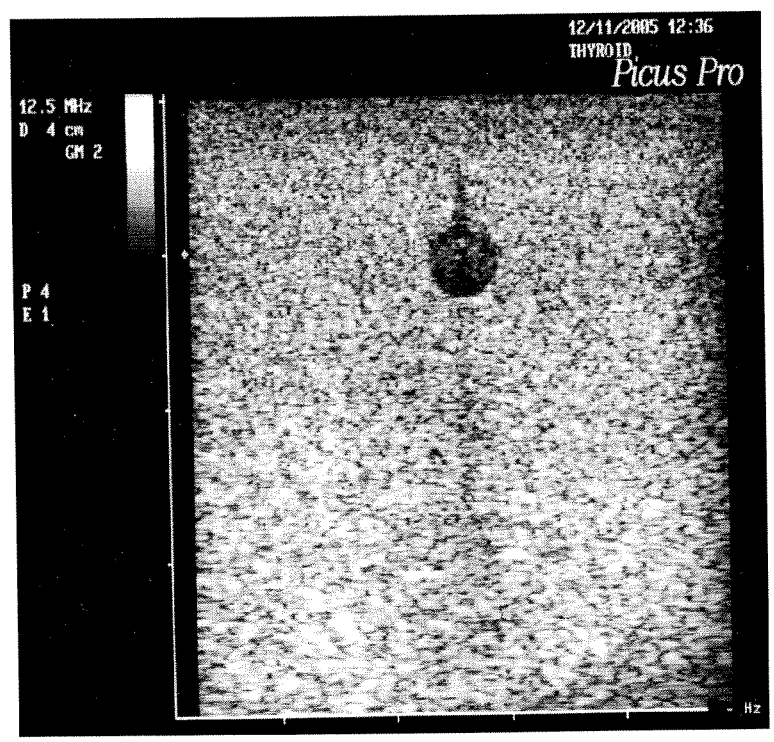

Experiments with the biopsy tool were carried out on Nodule #2, the center depth of which is 10.2 mm below the phantom surface as shown in FIG. 20(b). Two types of experiments were done: (i) inserting the Biopsy Tool needle into the breast phantom tissue only, and (ii) inserting the needle into the breast phantom tissue and then into Nodule #2. The screen prints from an HP4195 Spectrum Analyzer for these experiments are shown in FIGS. 21(a) and 21(b), and the results are summarized in FIGS. 22(a)-(b) and 23(a)-(b).

Figure 21A:
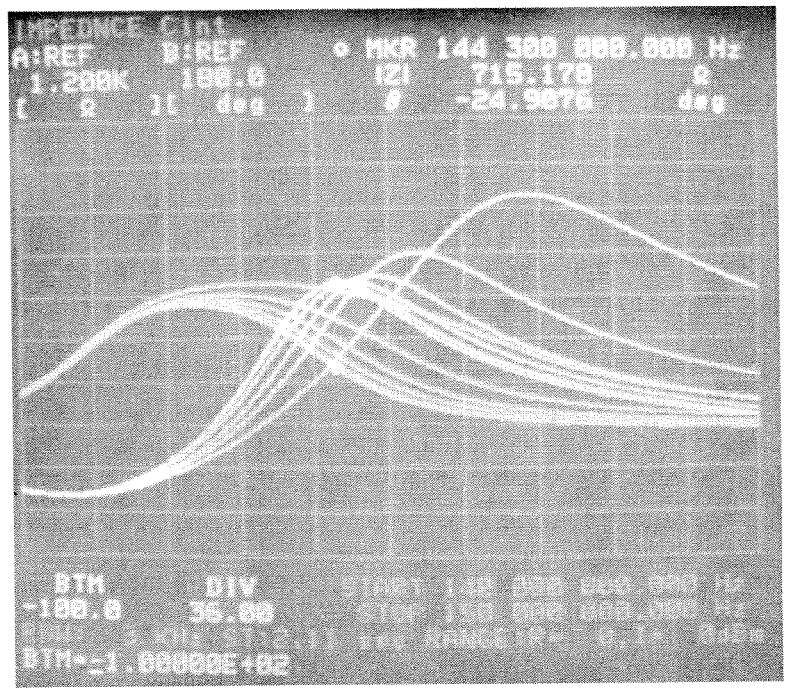
FIGS. 21(a), 21(b), 22(a), 22(b), 23(a), and 23(b) are graphs showing results of breast phantom experiments.
Figure 21B:
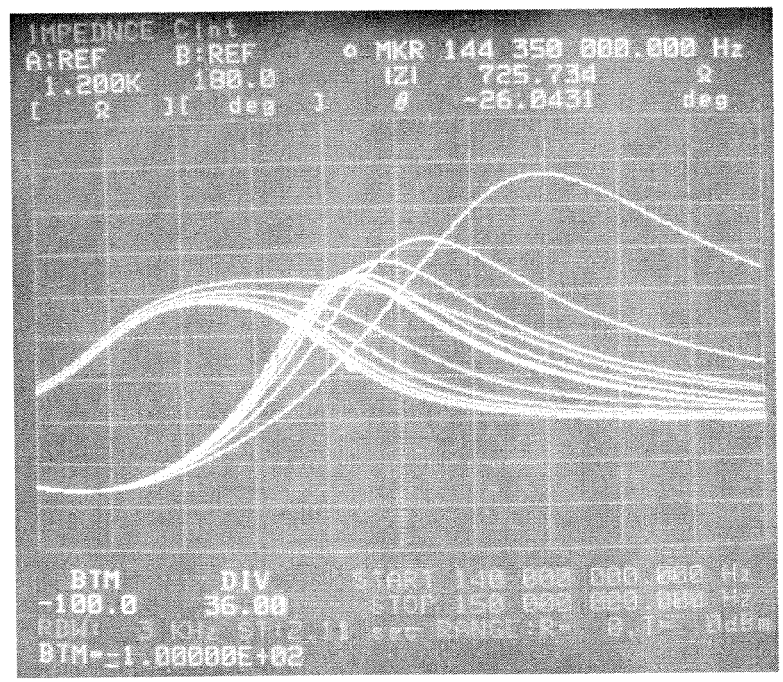

As shown in FIGS. 21(a)-(b) and the HP4195 spectrum analyzer screen print, the yellow (lighter) curves depict frequency sweep of impedance magnitude, while the blue (darker) curves depict frequency sweep of impedance phase. FIG. 21(a) shows the result of the experiment with the biopsy tool needle going into the breast phantom only, with no nodule targets during the procedure. FIG. 21(b) shows the result of the experiment with the biopsy tool needle going into the breast phantom and then into Nodule #2.

Figure 22A:
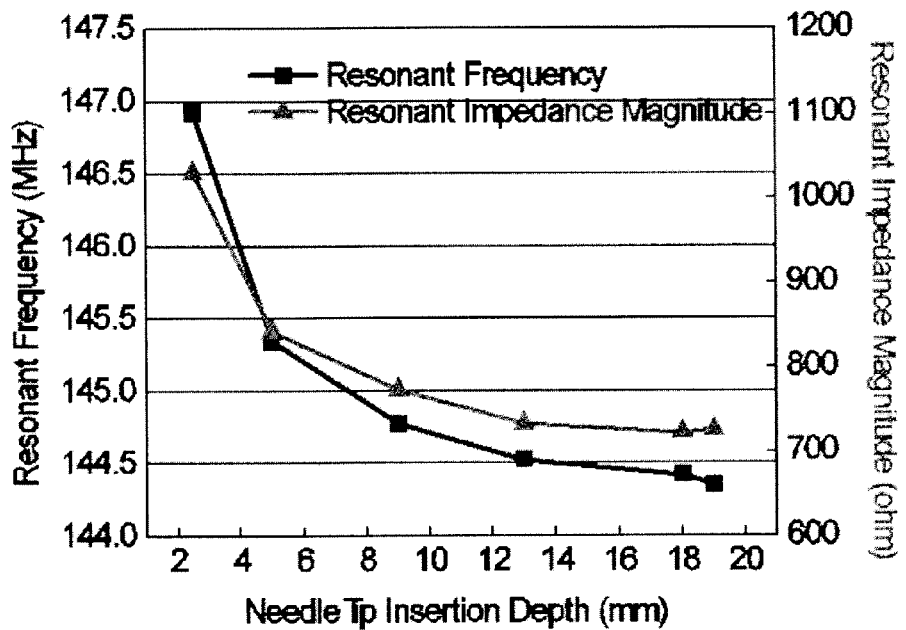
Figure 22B:
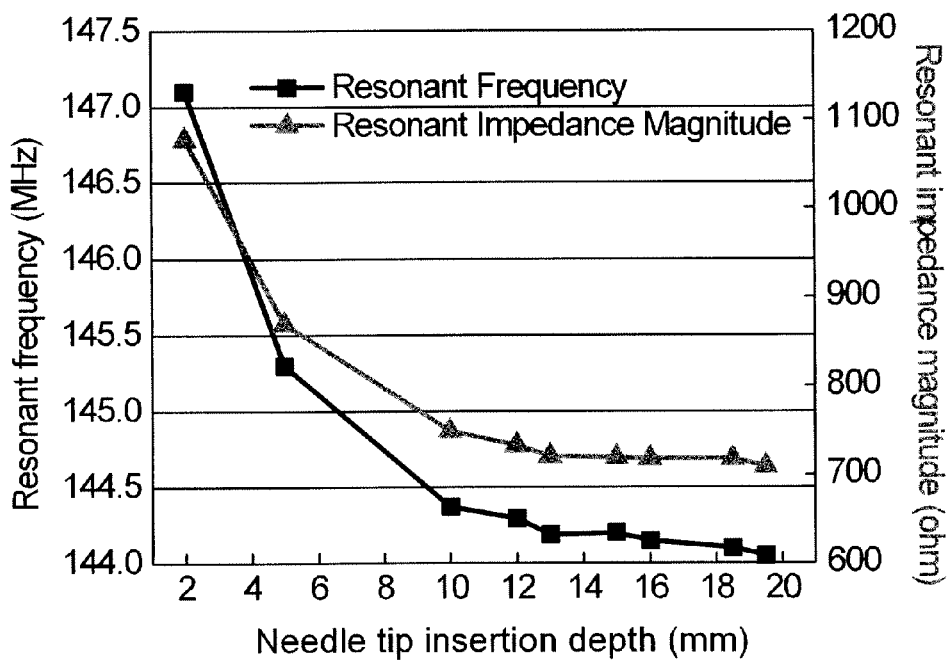

Turning to FIGS. 22(a)-(b), the plot shows a change of resonant frequency and impedance magnitude vs. needle tip insertion depth during the Biopsy Tool experiments is shown. Specifically. FIG. 22(a) shows the result of the experiment with the biopsy tool needle going into the breast phantom only, with no nodule targets during the procedure. FIG. 22(b) shows the result of the experiment with the biopsy tool needle going into the breast phantom and then into Nodule #2.

Figure 23A:
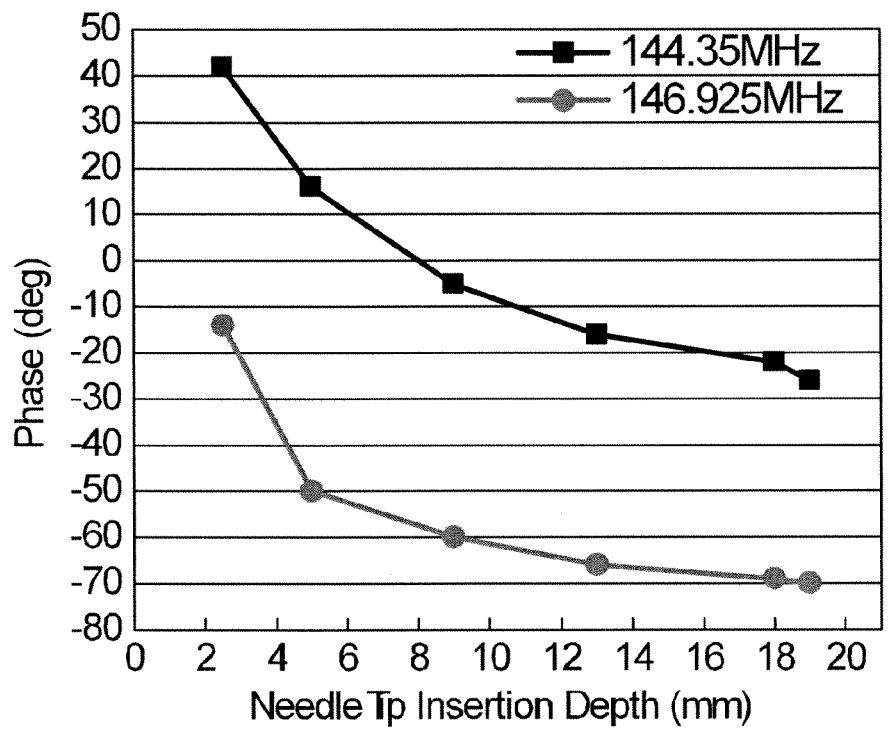
Figure 23B:
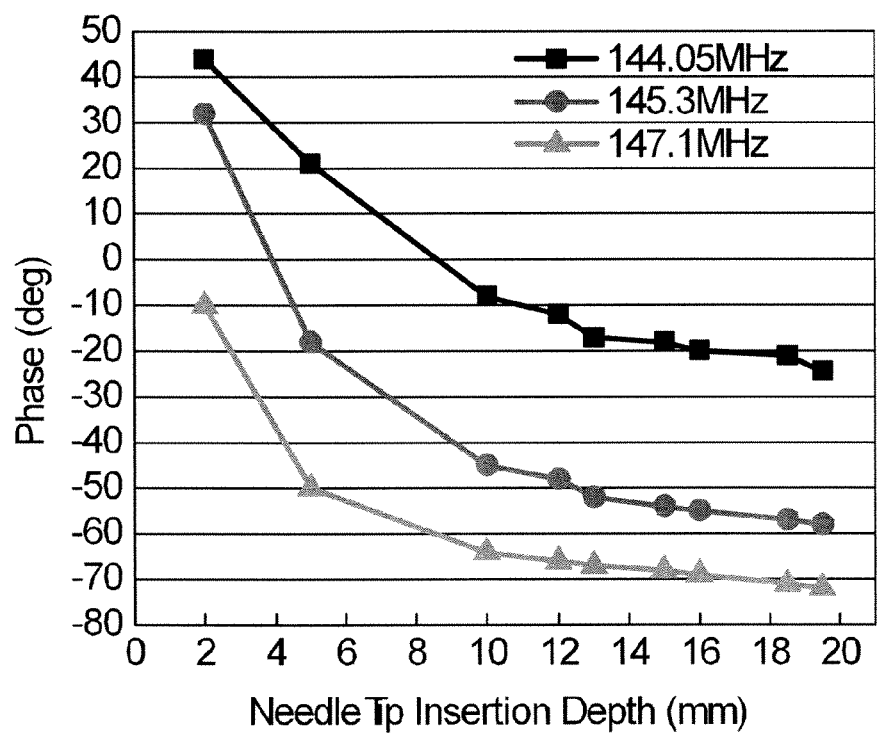

Turning to FIGS. 23(a)-(b), a change of impedance phase at a specific frequency vs. needle tip insertion depth during the Biopsy Tool experiments is shown. Specifically. FIG. 23(a) shows the result of the experiment with the biopsy tool needle going into the breast phantom only, with no nodule targets during the procedure. FIG. 23(b) shows the result of the experiment with the biopsy tool needle going into the breast phantom and then into Nodule #2.

The repeatable results of the foregoing biopsy tool experiments on breast phantom shown above indicate that the manner in which the biopsy tool provides differentiates the breast phantom tissue and the artificial nodule targets. By comparing the curves in FIGS. 22(a) and (b), it can be seen that the resonant frequency drops more when the needle goes through Nodule #2 on the insertion path (FIG. 22(b)), while the change of the resonant impedance magnitude remains almost the same as that in FIG. 22(a).

It is also notable that this differentiation is less significant compared with the results obtained in either the above-described gel-pad/olive or the pork tissue experiments. The change of impedance characteristics when the needle goes into the nodule target from the breast phantom tissue is less significant, and may not sufficiently clearly indicate the tissue contrast during an actual biopsy procedure. In these and other cases (e.g., where magnitude changes are small), alternative embodiments of the disclosed tool may be utilized. Such embodiments may, in general, include and present multiple sensors for tissue analysis. The data generated by the multiple sensors may be processed in a number of ways to improve resolution. For example, the multiple sensors may be implemented in differential mode to remove any common mode noise signals that would otherwise frustrate the analysis of data returned from a single sensor embodiment.

In some embodiments, an interface circuit may be integrated with the disclosed sensor devices by, for example, disposing the circuit in the needle cavity or elsewhere on the needle. The interface circuit may provide multiplexed communication, power, and/or an RF link to an external transceiver. In these ways, the interface circuit may reduce the lead count through the lumen. The circuit may also provide buffering, filtering, amplification and other signal conditioning functions locally for the sensor devices to support signal transmission to and from the sensor device.

In some embodiments, an interface circuit may dynamically convert the resonance-shifting characteristics of a PZT disc into a form that can then be easily processed to provide a differential signal. For instance, in implementations where tissue changes cause frequency resonance characteristics changes, an interface circuit may be capable of tracking the resonance frequency shift of the piezoelectric sensor. Such an interface circuit may generate an indicator of the resonance frequency, such as a clock signal with a clock frequency that varies according to the resonance frequency.

In some implementations, it may be useful to utilize a differential sensor device that employs two sensors such as described above. The output signals from the interface circuits of each sensor in a differential configuration can then be fed to an external analysis device. For example, if the outputs of the interface circuits include clock signals with clock frequencies that vary according to the resonance frequency, the outputs of the interface circuits may be coupled to a frequency mixer followed by a filter to obtain the frequency difference, which can be read out by a frequency counter. A frequency mixer and counter can be easily integrated with other signal processing circuits if needed. As another example, a clock signal at various tracked frequencies can be converted into voltage signals and read into a computing device for further processing.

Figure 24:
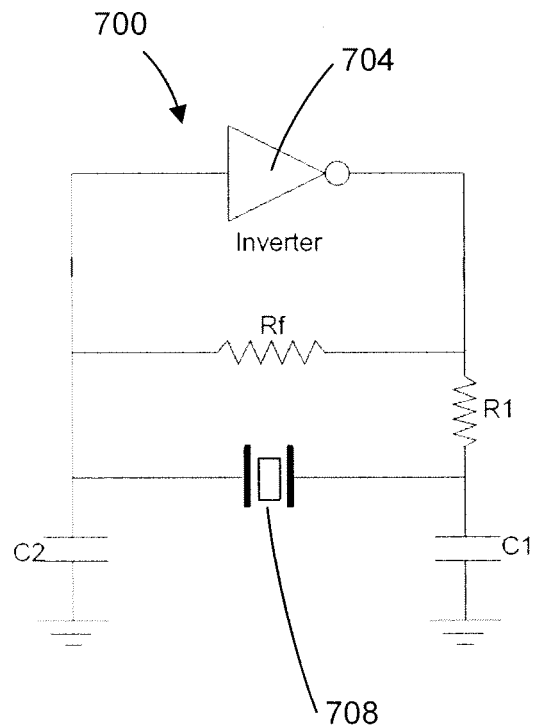
FIG. 24 is a diagram of an example interface circuit.

In some implementations, an interface circuit comprises an oscillating circuit with an oscillating frequency that changes based on the PZT disc. Similar to a quartz crystal which can be used as a frequency reference for electronic oscillating circuits, a PZT sensor can be measured in a similar way, while quality factor Q of its resonance would change when the sensor contacts tissue samples, thus affecting the sensitivity of the device. FIG. 24 is a diagram of an example oscillating circuit 700 based on a CMOS inverter 704 and a PZT disc 708. In this circuit, the inverter provides a phase shift of approximately 180° from input to output, and the network formed by the crystal, R1, C1, and C2 provides another 180° phase shift, making the total phase shift around the loop to be 360°. Simulation of this circuit indicated that, due to limitations of the inverter amplifier bandwidth resulting from limitations in CMOS process parameters, the higher frequency modes of the PZT resonator may not work. It is believed that replacing $R_1$ with a capacitor $C_{R1}$, at least in some implementations, may alleviate this problem and also may retain the benefits of $R_1$ such as limiting the driving level of the PZT resonator.

In other implementations, a crystal oscillator circuit can also be built using BJT transistors. In still other implementations, an oscillator circuit may utilize a phase-locked loop (PLL) to track the resonance frequency of the sensor.

Figure 25:
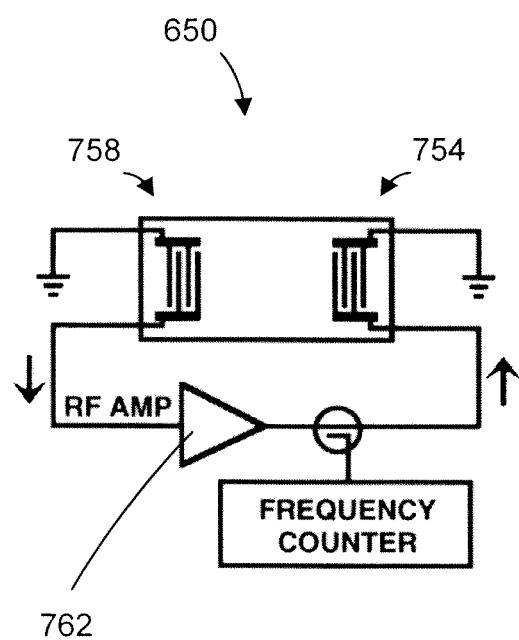
FIG. 25 is a diagram of another example interface circuit.

An oscillator circuit may also be based on a surface acoustic wave (SAW) device in which an elastic wave propagates near a stress-free surface of a piezoelectric plate. The finite propagation time from the moment the wave is generated until it reaches a detector is called its time delay. Small changes in the surface composition, such as added mass by surface adsorption, cause changes in the wave propagation speed, which can be detected as changes in the time delay. As this change is very small for SAW sensors, a delay line oscillation can be formed. FIG. 25 is a diagram of an example oscillator circuit 750 utilizing a SAW device. An electrode array 754, which may be referred to as an interdigital transducer (IDT), is used as a generator and converts an electric signal into SAW which is detected and converted back to an electric signal by another IDT 758. This detected signal is amplified and applied to the generator (754), and thus a delay line closed loop is formed. Using an amplifier 762 with appropriate gain, this delay line oscillates at a frequency which depends on physical parameters such as the electrode spacings of the IDTs 754 and 758, thus converting the variations in time delay to variations in oscillation frequency.

A SAW device has a high sensitivity and can tolerate a thin coating which can be a protection layer. It can also be configured in differential mode, which will be described below. The SAW device can be fabricated by using μUSM to make a PZT plate. The IDT arrays can then be added by sputtering and etching with a mask, and the amplifier on a silicon die can be bonded underneath the PZT plate. The operating frequency ($f_0$) of a SAW device is given by $$f_0 = \frac{V}{a},$$

where V is the speed of Rayleigh surface wave in the plate and a is the electrode spacing of the IDT.

In some implementations, it may be useful to increase detected resonance shifts and/or decrease performance degradation due to signal attenuation and/or stray capacitances. Signal attenuation and/or stray capacitances may be made worse because of the type of tissue and/or the depth of the needle within the tissue, for example.

Figure 26:
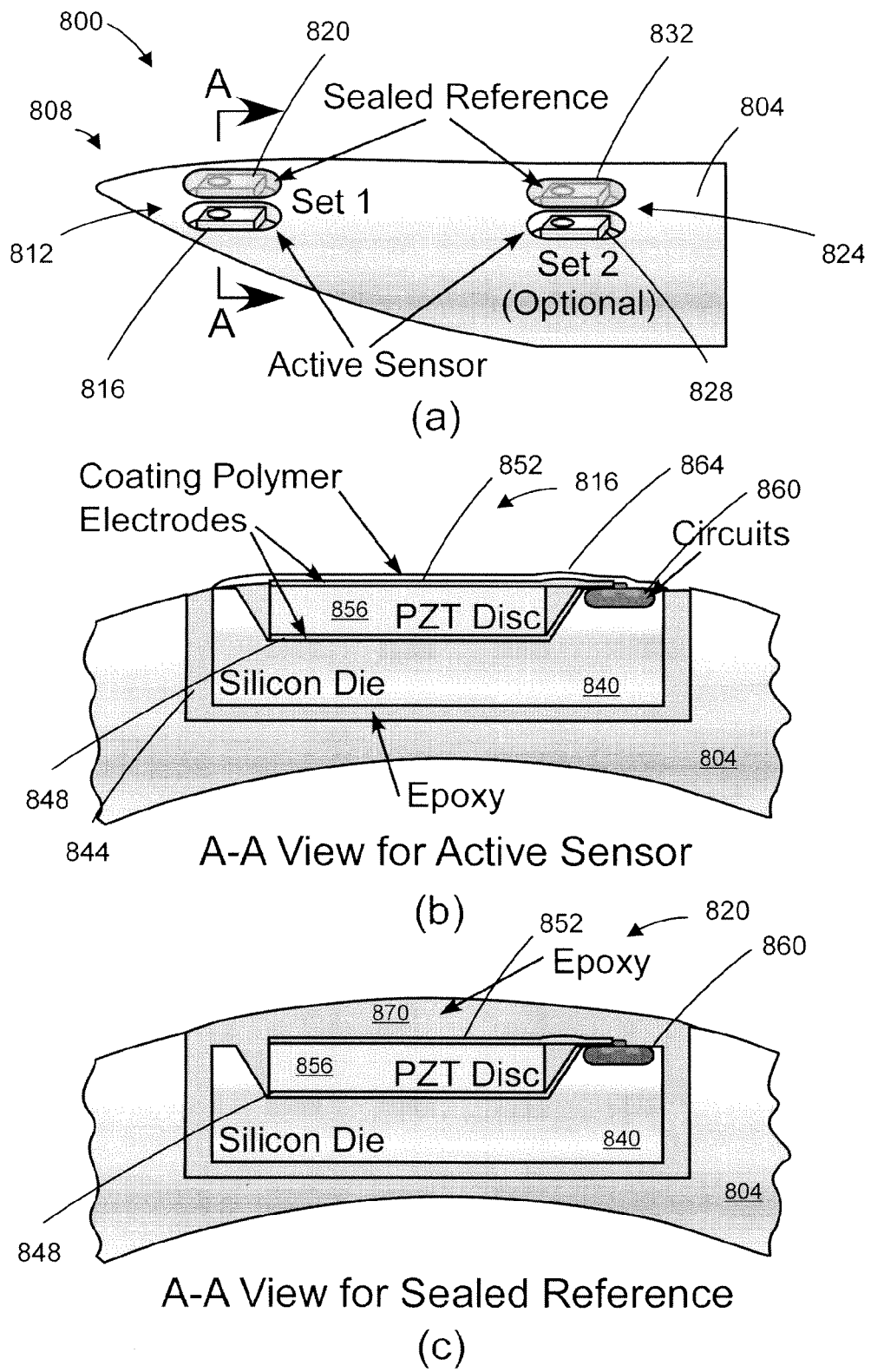
FIGS. 26(a), (b), and (c) are diagrams of an example biopsy device having multiple sensors.

In some implementations, a plurality of sensors may be mounted on the biopsy tool. For example, two sensors may be utilized to provide a differential measurement. As another example, one sensor may be utilized for sensing and another sensor may be utilized as a reference. FIG. 26(a) is a diagram of an example biopsy tool 800 employing a plurality of sensors. In this example, a set 812 of two sensors can be integrated on a needle tube 804 proximate to a tip 808 of the needle 804. One sensor 816 actively measures the tissue characteristics, while the other sensor 820 is sealed in acoustic insulating material such as epoxy or polystyrene. This configuration can be used to reduce any common mode changes in the sensor response caused by parasitic capacitance and other interference from the human body, etc.

Optionally, as shown in FIG. 26(a), another set 824 of two sensors with the same (or similar) configuration as the set 812 can be integrated on the needle tube 804 at a distance from the set 812 and further from the tip 808 than the set 812. In this example, at the tissue interface the set 812 of sensors can be inside the target tissue and the other set 824 of sensors may be outside of the target tissue, providing tissue contrast by the differential readout between the two sets 812 and 824. As shown in the cross sectional A-A view for the active sensor 816 in FIG. 26(b), the sensor 816 may be mounted in an etched cavity of the needle 804. The sensor 816 may comprise a silicon die 840 held within the cavity by an epoxy 844. The sensor may include a PZT disk 856 having two electrodes 848 and 852. The PZT disk 856 may be mounted to the silicon die 840. A circuit 860 also may be mounted to the silicon die 840. The circuit 860 may include an interface circuit and/or an amplification circuit, for example. A thin polymer coating 864, such as parylene, can be applied to insulate the whole sensor device 816. A reference sensor sealed by acoustic insulating material 870 such as epoxy or polystyrene is shown in FIG. 26(c).

As can be seen in FIGS. 26(b) and 26(c), a sensor and an associated interface circuit can be mounted on a common substrate such as a silicon substrate. Optionally, a sensor and an associated interface circuit can be separately mounted to a needle. For example, the associated interface circuit could be mounted to the needle at a location further removed from the tip of the needle as compared to the sensor.

A plurality of different types of sensors also may be utilized. For example, a plurality of sensors can be included in a silicon substrate and integrated on the biopsy needle to provide complementary tissue characteristics. In one example, an electrode array for voltammetry or potentiometry may be utilized to monitor the ionic concentration in the diseased tissues, and one or more PZT sensors such as describe above may be utilized to measure resonance changes. One of ordinary skill in the art will recognize many other types of sensors and combinations of sensors may be utilized.

Although devices and techniques described above were in the context of biopsies, one of ordinary skill in the art will recognize that these techniques can be utilized in other contexts as well. For example, similar devices could be used to guide a delivery system, such as a drug delivery system, to a target tissue. For example, one or more sensors could mounted proximate to the tip of a needle used to deliver a substance to a target tissue. Similarly, one or more sensors could be mounted proximate to a tip of some other surgical tool to assist in guiding the tip to a target tissue.

Properties or changes in properties sensed by the sensor(s) could be indicated to a physician, technician, etc., in a variety of ways. For example, properties or changes in properties could be indicated visually, audibly, with force feedback, etc. A computing device could be communicatively coupled to the sensors and/or to an interface device or devices (which is in turn communicatively coupled to the sensor(s)). The communication device could generate indications based on the properties or changes in properties sensed by the sensor(s).

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

The invention claimed is:

1. A needle comprising:
 a tube having disposed at one end a tip designed for passing through one or more tissues to reach a target tissue; and
 a first sensor mounted to the needle at a location proximate to the tip, the sensor within a cavity formed in a wall of the needle, the sensor mounted to the wall of the needle, and operable to detect a tissue density of tissue in contact with the tip as the needle passes through the one or more tissues;
 wherein an oscillatory response of the sensor indicates a change in tissue density of the tissue in contact with the tip as the tip passes from one tissue to the target tissue.

2. A needle according to claim 1, wherein the first sensor is a first piezoelectric sensor.

3. A needle according to claim 1, further comprising a communication link operable to communicate a signal from the first sensor to an analysis device.

4. A needle according to claim 1, wherein the first sensor comprises a resonant sensor, wherein changes in a resonance frequency of the first sensor indicate changes in density of tissue in contact with the first sensor.

5. A needle according to claim 1, further comprising a second sensor disposed in the tip at a location proximate the first sensor, the first and second sensors operative collectively to eliminate common mode changes in sensor response.

6. A needle according to claim 5, wherein the second sensor is sealed in an acoustically isolating material.

7. A needle according to claim 1, further comprising a second sensor mounted to the needle at a distance from the tip greater than that of the first sensor, the first and second sensors arranged to detect an interface between two tissues.

8. A needle according to claim 1, wherein the sensor is a lead zirconate titanate (PZT) sensor.

9. A needle according to claim 8, wherein the PZT sensor is a PZT disk.

10. A needle according to claim 8, wherein the PZT sensor is mounted within a cavity formed on a wall of the needle proximate to the tip.

11. A needle according to claim 10, wherein a wall of the cavity acts as a diaphragm associated with the PZT sensor.

12. A needle according to claim 1, further comprising an epoxy filling the cavity in which the first sensor is mounted.

13. A needle according to claim 1, wherein the wall of the needle into which the cavity is formed acts as a diaphragm.

14. A system for use while guiding a needle tip to a target tissue, the system comprising:
 a needle having a tube and the tip, tip disposed at one end of the tube and designed for passing through one or more tissues to reach the target tissue;
 a first sensor mounted to the needle at a location proximate to the tip, the sensor within a cavity formed in a wall of the needle, the sensor mounted to the wall of the needle, and operable to detect a tissue density of tissue in contact with the tip as the needle passes through the one or more tissues;
 an analysis unit operable to detect and analyze in real time a first oscillatory response signal from the first sensor, the first oscillatory response signal indicative of tissue density of the tissue in contact with the tip, and further operable to allow an operator to guide the needle tip to the target tissue; and
 a communication link communicatively coupling the first sensor to the analysis unit.

15. A system according to claim 14, wherein the analysis unit comprises a signal analyzer.

16. A system according to claim 14, wherein the first sensor is a first piezoelectric sensor.

17. A system according to claim 14, wherein the first sensor comprises a resonant sensor, wherein changes in a resonance frequency of the first sensor indicate changes in density of tissue in contact with the first sensor.

18. A system according to claim 14, further comprising a second sensor disposed in the tip at a location proximate the first sensor, the second sensor communicatively coupled to the analysis unit by the communication link and providing a second signal to the analyzer unit;
 wherein the analyzer unit analyzes the first and second signals to eliminate common mode changes in responses of the first and second sensors.

19. A system according to claim 14, wherein the first sensor is a piezoelectric sensor comprising a lead zirconate titanate (PZT) disk.

20. A system according to claim 14, further comprising an epoxy filling the cavity in which the first sensor is mounted.

21. A system according to claim 14, wherein the wall of the needle into which the cavity is formed acts as a diaphragm.

22. A method of positioning a needle tip in contact with a target tissue, the method comprising:
 inserting a needle through the tissues of a patient;
 receiving a signal from a sensor fixedly mounted to an interior surface of a cavity formed in the wall of the needle at a location proximate the tip of the needle;
 analyzing the signal in real time to determine an oscillatory response of the sensor indicative of the tissue density of a tissue in contact with the tip of the needle; and
 determining that the tip of the needle is in contact with the target tissue according to the analyzed signal.

23. A method according to claim 22, wherein determining that the tip of the needle is in contact with the target tissue according to the analyzed signal comprises detecting a change in the analyzed signal greater than a threshold value.

24. A method according to claim 22, wherein analyzing a signal received from a sensor comprises analyzing a measured resonance frequency of the sensor, the resonance frequency changing in response to density of tissue proximate the sensor.

25. A method according to claim 22, wherein the sensor is a piezoelectric sensor comprising a lead zirconate titanate (PZT) disk.

* * * * *